US012637504B2

(12) United States Patent
Matono et al.

(10) Patent No.: US 12,637,504 B2
(45) Date of Patent: *May 26, 2026

(54) HUMANIZED ANTIBODY AND METHOD FOR USING THE SAME

(71) Applicant: Nihon Medi-Physics Co., Ltd., Tokyo (JP)

(72) Inventors: Mitsuhiro Matono, Suita (JP); Jun Sakai, Takarazuka (JP); Toru Nagai, Osaka (JP); Naoki Tanuma, Osaka (JP); Richard Buick, Belfast (GB)

(73) Assignee: Nihon Medi-Physics Co., Ltd., Tokyo (JP)

( * ) Notice: Subject to any disclaimer, the term of this patent is extended or adjusted under 35 U.S.C. 154(b) by 730 days.

This patent is subject to a terminal disclaimer.

(21) Appl. No.: 17/430,704

(22) PCT Filed: Oct. 16, 2020

(86) PCT No.: PCT/JP2020/039075
§ 371 (c)(1),
(2) Date: Aug. 12, 2021

(87) PCT Pub. No.: WO2021/075545
PCT Pub. Date: Apr. 22, 2021

(65) Prior Publication Data
US 2022/0144927 A1 May 12, 2022

(30) Foreign Application Priority Data
Oct. 18, 2019 (JP) ................................. 2019-191560

(51) Int. Cl.
*C07K 16/18* (2006.01)
*A61P 35/00* (2006.01)
(Continued)

(52) U.S. Cl.
CPC .............. *C07K 16/18* (2013.01); *A61P 35/00* (2018.01); *G01N 33/532* (2013.01); *G01N 33/577* (2013.01); *C07K 2317/24* (2013.01)

(58) Field of Classification Search
CPC .... C07K 16/18; C07K 16/3092; C07K 16/46; C07K 2317/24; C07K 2317/94;
(Continued)

(56) References Cited

U.S. PATENT DOCUMENTS

2012/0141375 A1* 6/2012 Gold .................... A61K 51/109
424/9.34
2012/0226119 A1 9/2012 Dobosz et al.

FOREIGN PATENT DOCUMENTS

JP 7-203974 A 8/1995
JP 11-5749 A 1/1999
(Continued)

OTHER PUBLICATIONS

Chiu, M.L., et al (2019) Antibody structure and function: The basis for engineering therapeutics Antibodies 8(55); 1-80 (Year: 2019).*
(Continued)

*Primary Examiner* — Scarlett Y Goon
*Assistant Examiner* — Audrey L Buttice
(74) *Attorney, Agent, or Firm* — Lathrop GPM LLP; Malaika O. D. Tyson

(57) ABSTRACT

The present invention aims to provide a humanized antibody or an antigen-binding fragment thereof having stable physical property, superior in tumor accumulation, and capable of binding to mucin subtype 5AC.
The above-mentioned problem is solved by the present invention that provides a humanized antibody or an antigen-binding fragment thereof having a heavy chain variable region consisting of the amino acid sequence shown in SEQ ID NO: 1-4 or a mutated amino acid sequence thereof, and
(Continued)

[heavy chain variable region 1 (H01)]
EVQLLESGGGLVQPGGSLRLSCAAS*GFTFSNYGMS*WVR
QAPGKGLEWVS*TISNSGRYTY*FPDSVKG*RFTISRDNSK
NTLYLQMNSLRAEDTALYYC*TRHLDYANYDAMDY*WGQG
TLVTVSS
[heavy chain variable region 2 (H02)]
LVQLVESGGGVVRPGGSLRLSCAAS*GFTFSNYGMS*WIR
QAPGKGLEWVS*TISNSGRYTY*FPDSVKG*RFTISRDNAK
NSLYLQMNSLRAEDTALYYC*TRHLDYANYDAMDY*WGQG
TLVTVSS
[heavy chain variable region 3 (H03)]
LVQLVESGGGVVQPGKSLRLSCAAS*GFTFSNYGMS*WVR
QAPGKGLEWVA*TISNSGRYTY*FPDSVKG*RFTISRDNSK
NTLYLQMNSLRAEDTAVYYC*TRHLDYANYDAMDY*WGQG
TLVTVSS
[heavy chain variable region 4 (H04)]
EVQLLESGGGLVQPGGSLRLSCAVS*GFTFSNYGMS*WVR
QAPGKGLEWVS*TISNSGRYTY*FPDSVKG*RFTISRDNSK
NTLYLQMNTLRAEDTAVYYC*TRHLDYANYDAMDY*WGQG
TPVTVSS a light chain variable region consisting of the amino acid sequence shown in SEQ ID NO: 5-8 or a mutated amino acid sequence thereof, and capable of binding to mucin subtype 5AC.

15 Claims, 3 Drawing Sheets

Specification includes a Sequence Listing.

(51) Int. Cl.
*G01N 33/532* (2006.01)
*G01N 33/577* (2006.01)

(58) Field of Classification Search
CPC ... C07K 2317/73; A61P 35/00; G01N 33/532; G01N 33/577; G01N 33/57484; G01N 33/57407; G01N 33/53; G01N 2333/4725; C12N 5/10; C12N 15/63; C12N 5/0682; C12N 15/85; C12N 2510/00; C12N 2800/107; A61K 49/00; A61K 2039/505; A61K 39/395
See application file for complete search history.

(56) References Cited

FOREIGN PATENT DOCUMENTS

| | | | | |
|---|---|---|---|---|
| JP | 2012-532846 A | 12/2012 | | |
| WO | WO 2013/157102 A1 | 10/2013 | | |
| WO | WO-2013157105 A1 * | 10/2013 | .............. | A61P 35/00 |
| WO | WO 2026/003869 | 1/2016 | | |

OTHER PUBLICATIONS

Rabia, L.A. et al (2018) Understanding and overcoming trade-offs between antibody affinity, specificity, stability and solubility Biochem Eng J 137; 365-374 (Year: 2018).*

Van Scheltinga, A.G.T.T, et al (2011) Intraoperative near-infrared fluorescence tumor imaging with vascular endothelial growth factor and human epidermal growth factor receptor 2 targeting antibodies J. Nucl. Med 52; 1178-1785 (Year: 2011).*

Christensen, J., et al (2015) Non-invasive in vivo imaging and quantification of tumor growth and metastasis in rats using cells expressing far-red fluorescence protein PLOS One 10(7); e0132725; 1-14 (Year: 2015).*

Extended European Search Report issued in European Patent Application No. 20877846.4 on Oct. 9, 2023.

Tetsuji Sawada et al., "Immunotherapy for Pancreatic Cancer by Antibody Directed Against Mucin", Japanese Journal of Clinical Medicine, vol. 64, extra issue 1, 2006, pp. 274 278 (with English Translation).

Tetsuji Sawada, et al., "Preoperative Clinical Radioimmunodetection of Pancreatic Cancer by $^{111}$In-labeled Chimeric Monoclonal Antibody Nd2," Japanese Journal of Cancer Research, vol. 90, Oct. 1999, pp. 1179-1186.

Akimasa Inui, et al., "Radioimmunotherapy for Pancreatic Carcinoma Using [131]I-Labeled Monoclonal Antibody Nd2 in Xenografted Nude Mice," Japanese Journal of Cancer Research, vol. 87, Sep. 1996, pp. 977-984.

International Search Report issued on Dec. 22, 2020 in PCT/JP2020/039075 filed on Oct. 16, 2020, 2 pages.

Combined Chinese Office Action and Search Report issued May 25, 2025, (client received Jun. 27, 2025) in corresponding Chinese Patent Application No. 202080072096.6 (with English Translation), 28 pages.

Singaporean Written Opinion issued Jun. 20, 2025, (client received Jul. 2, 2025) in corresponding Singaporean Patent Application No. 11202203887U, 9 pages.

Vietnamese Office Action issued Aug. 14, 2025, (client received on Sep. 29, 2025) in corresponding Vietnamese Patent Application No. 1-2022-03103 (with English Translation), 6 pages.

* cited by examiner

Fig. 1

[heavy chain variable region 1 (H01)]
EVQLLESGGGLVQPGGSLRLSCAASGFTFSNYGMSWVR
QAPGKGLEWVSTISNSGRYTYEPDSVKGRFTISRDNSK
NTLYLQMNSLRAEDTALYYCTRHLDYANYDAMDYWGQG
TLVTVSS
[heavy chain variable region 2 (H02)]
LVQLVESGGGVVRPGGSLRLSCAASGFTFSNYGMSWIR
QAPGKGLEWVSTISNSGRYTYEPDSVKGRFTISRDNAK
NSLYLQMNSLRAEDTALYYCTRHLDYANYDAMDYWGQG
TLVTVSS
[heavy chain variable region 3 (H03)]
LVQLVESGGGVVQPGRSLRLSCAASGFTFSNYGMSWVR
QAPGKGLEWVATISNSGRYTYEPDSVKGRFTISRDNSK
NTLYLQMNSLRAEDTAVYYCTRHLDYANYDAMDYWGQG
TLVTVSS
[heavy chain variable region 4 (H04)]
EVQLLESGGGLVQPGGSLRLSCAVSGFTFSNYGMSWVR
QAPGKGLEWVSTISNSGRYTYEPDSVKGRFTISRDNSR
NTLYLQMNTLRAEDTAVYYCTRHLDYANYDAMDYWGQG
TPVTVSS

Fig. 2

[light chain variable region 1 (L01)]
DIVMTQSPSSLSASVGDRVTITCRASKSVTTSDFSYMH
WYQQKPGKAPKLLIYLASNLESGVPSRFSGSGSGTDFT
LTISSLQPEDFATYYCQHSREFPWTFGGGTKVEIK
[light chain variable region 2 (L02)]
DVVMTQSPSTLSASVGDRVTITCRASKSVTTSDFSYMH
WYQQKPGQAPKLLIYLASNLESGVPSRFSGSGSGTDFT
LTISSLQPEDFATYYCQHSREFPWTFGQGTKLEIK
[light chain variable region 3 (L03)]
DIQMTQSPSSLSASVGDRVTITCRASKSVTTSDFSYMH
WYQQKPGKSPKLLIYLASNLESGVPSRFSGSGSGTDFS
LTISSLQPEDFATYYCQHSREFPWTFGGGTKVEIK
[light chain variable region 4 (L04)]
DIVMTQSPDSLAVSLGERATINCKASKSVTTSDFSYLH
WYQQKPGQPPKLLIYLASNLESGVPDRFSGSGSGTDFT
LTISSLQAEDVAVYYCQHSREFPWTFGGGTKLEIK

Fig. 3

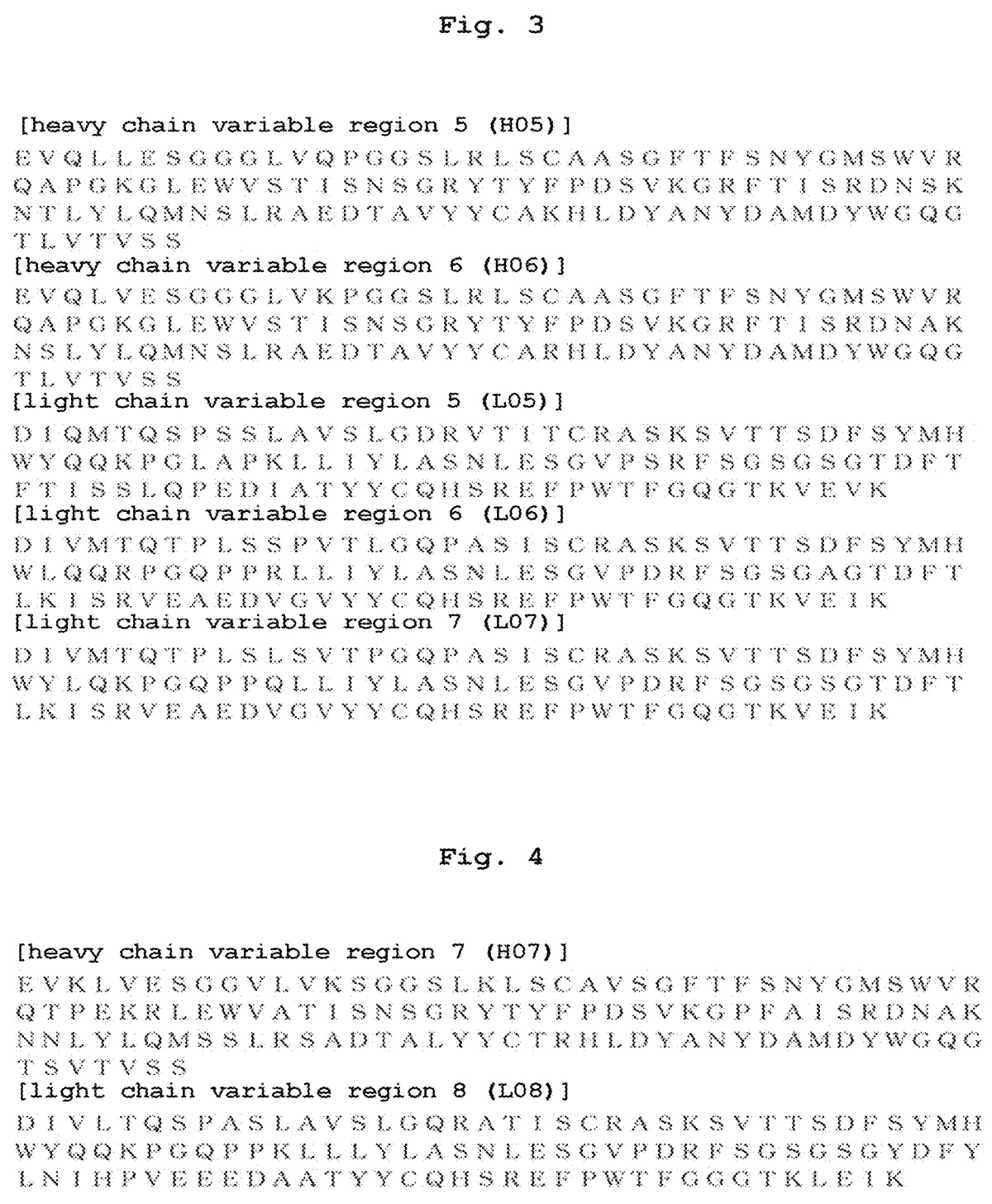

[heavy chain variable region 5 (H05)]
E V Q L L E S G G G L V Q P G G S L R L S C A A S G F T F S N Y G M S W V R
Q A P G K G L E W V S T I S N S G R Y T Y F P D S V K G R F T I S R D N S K
N T L Y L Q M N S L R A E D T A V Y Y C A K H L D Y A N Y D A M D Y W G Q G
T L V T V S S
[heavy chain variable region 6 (H06)]
E V Q L V E S G G G L V K P G G S L R L S C A A S G F T F S N Y G M S W V R
Q A P G K G L E W V S T I S N S G R Y T Y F P D S V K G R F T I S R D N A K
N S L Y L Q M N S L R A E D T A V Y Y C A R H L D Y A N Y D A M D Y W G Q G
T L V T V S S
[light chain variable region 5 (L05)]
D I Q M T Q S P S S L A V S L G D R V T I T C R A S K S V T T S D F S Y M H
W Y Q Q K P G L A P K L L I Y L A S N L E S G V P S R F S G S G S G T D F T
F T I S S L Q P E D I A T Y Y C Q H S R E F P W T F G Q G T K V E V K
[light chain variable region 6 (L06)]
D I V M T Q T P L S S P V T L G Q P A S I S C R A S K S V T T S D F S Y M H
W L Q Q R P G Q P P R L L I Y L A S N L E S G V P D R F S G S G A G T D F T
L K I S R V E A E D V G V Y Y C Q H S R E F P W T F G Q G T K V E I K
[light chain variable region 7 (L07)]
D I V M T Q T P L S L S V T P G Q P A S I S C R A S K S V T T S D F S Y M H
W Y L Q K P G Q P P Q L L I Y L A S N L E S G V P D R F S G S G S G T D F T
L K I S R V E A E D V G V Y Y C Q H S R E F P W T F G Q G T K V E I K

Fig. 4

[heavy chain variable region 7 (H07)]
E V K L V E S G G V L V K S G G S L K L S C A V S G F T F S N Y G M S W V R
Q T P E K R L E W V A T I S N S G R Y T Y F P D S V K G P F A I S R D N A K
N N L Y L Q M S S L R S A D T A L Y Y C T R H L D Y A N Y D A M D Y W G Q G
T S V T V S S
[light chain variable region 8 (L08)]
D I V L T Q S P A S L A V S L G Q R A T I S C R A S K S V T T S D F S Y M H
W Y Q Q K P G Q P P K L L L Y L A S N L E S G V P D R F S G S G S G Y D F Y
L N I H P V E E E D A A T Y Y C Q H S R E F P W T F G G G T K L E I K

SEQUENCE LISTING

```
<160> NUMBER OF SEQ ID NOS: 15

<210> SEQ ID NO 1
<211> LENGTH: 121
<212> TYPE: PRT
<213> ORGANISM: Artificial Sequence
<220> FEATURE:
<223> OTHER INFORMATION: Humanized antibody heavy chain variable region
      1 (H01)

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Gly Met Ser Trp Val Arg Gln Ala Pro Gly Lys Gly Leu Glu Trp Val
        35                  40                  45

Ser Thr Ile Ser Asn Ser Gly Arg Tyr Thr Tyr Phe Pro Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Thr Arg His Leu Asp Tyr Ala Asn Tyr Asp Ala Met Asp Tyr Trp Gly
                100                 105                 110

Gln Gly Thr Leu Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: Humanized antibody heavy chain variable region
      2 (H02)

<400> SEQUENCE: 2

Leu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Ser Asn Tyr
        20                  25                  30

Gly Met Ser Trp Ile Arg Gln Ala Pro Gly Lys Gly Leu Glu Trp Val
        35                  40                  45

Ser Thr Ile Ser Asn Ser Gly Arg Tyr Thr Tyr Phe Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Arg His Leu Asp Tyr Ala Asn Tyr Asp Ala Met Asp Tyr Trp Gly
                100                 105                 110

Gln Gly Thr Leu Val Thr Val Ser Ser
        115                 120

<210> SEQ ID NO 3
<211> LENGTH: 121
<212> TYPE: PRT
<213> ORGANISM: Artificial Sequence
<220> FEATURE:
<223> OTHER INFORMATION: Humanized antibody heavy chain variable region
      3 (H03)

<400> SEQUENCE: 3

Leu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
        20                  25                  30

Gly Met Ser Trp Val Arg Gln Ala Pro Gly Lys Gly Leu Glu Trp Val
        35                  40                  45

Ala Thr Ile Ser Asn Ser Gly Arg Tyr Thr Tyr Phe Pro Asp Ser Val
        50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Thr Arg His Leu Asp Tyr Ala Asn Tyr Asp Ala Met Asp Tyr Trp Gly
            100                 105                 110

Gln Gly Thr Leu Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: Humanized antibody heavy chain variable region
      4 (H04)

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Thr Ile Ser Asn Ser Gly Arg Tyr Thr Tyr Phe Pro Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Thr Leu Arg Ala Glu Asp Thr Ala Val Tyr Tyr Cys
                85                  90                  95

Thr Arg His Leu Asp Tyr Ala Asn Tyr Asp Ala Met Asp Tyr Trp Gly
            100                 105                 110

Gln Gly Thr Pro Val Thr Val Ser Ser
        115                 120

<210> SEQ ID NO 5
<211> LENGTH: 111
<212> TYPE: PRT
<213> ORGANISM: Artificial Sequence
<220> FEATURE:
<223> OTHER INFORMATION: Humanized antibody light chain variable region
      1 (L01)

<400> SEQUENCE: 5

Asp Ile Val Met Thr Gln Ser Pro Ser Ser Leu Ser Ala Ser Val Gly
1               5                   10                  15

Asp Arg Val Thr Ile Thr Cys Arg Ala Ser Lys Ser Val Thr Thr Ser
            20                  25                  30

Asp Phe Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gly Gly Thr Lys Val Glu Ile Lys
            100                 105                 110

<210> SEQ ID NO 6
<211> LENGTH: 111
```

-continued

```
<212> TYPE: PRT
<213> ORGANISM: Artificial Sequence
<220> FEATURE:
<223> OTHER INFORMATION: Humanized antibody light chain variable region
      2 (L02)

<400> SEQUENCE: 6

Asp Val Val Met Thr Gln Ser Pro Ser Thr Leu Ser Ala Ser Val Gly
1               5                   10                  15

Asp Arg Val Thr Ile Thr Cys Arg Ala Ser Lys Ser Val Thr Thr Ser
            20                  25                  30

Asp Phe Ser Tyr Met His Trp Tyr Gln Gln Lys Pro Gly Gln Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Leu Glu Ile Lys
            100                 105                 110

<210> SEQ ID NO 7
<211> LENGTH: 111
<212> TYPE: PRT
<213> ORGANISM: Artificial Sequence
<220> FEATURE:
<223> OTHER INFORMATION: Humanized antibody light chain variable region
      3 (L03)

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Thr Thr Ser
            20                  25                  30

Asp Phe Ser Tyr Met His Trp Tyr Gln Gln Lys Pro Gly Lys Ser Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Ser Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gly Gly Thr Lys Val Glu Ile Lys
            100                 105                 110

<210> SEQ ID NO 8
<211> LENGTH: 111
<212> TYPE: PRT
<213> ORGANISM: Artificial Sequence
<220> FEATURE:
<223> OTHER INFORMATION: Humanized antibody light chain variable region
      4 (L04)

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ala Ser Lys Ser Val Thr Thr Ser
            20                  25                  30

Asp Phe Ser Tyr Leu His Trp Tyr Gln Gln Lys Pro Gly Gln Pro Pro
```

-continued

```
         35                40                45

Lys Leu Leu Ile Tyr Leu Ala Ser Asn Leu Glu Ser Gly Val Pro Asp
     50                55                60

Arg Phe Ser Gly Ser Gly Ser Gly Thr Asp Phe Thr Leu Thr Ile Ser
65                70                75                80

Ser Leu Gln Ala Glu Asp Val Ala Val Tyr Tyr Cys Gln His Ser Arg
                  85                90                95

Glu Phe Pro Trp Thr Phe Gly Gly Gly Thr Lys Leu Glu Ile Lys
              100                105                110

<210> SEQ ID NO 9
<211> LENGTH: 121
<212> TYPE: PRT
<213> ORGANISM: Artificial Sequence
<220> FEATURE:
<223> OTHER INFORMATION: Humanized antibody heavy chain variable region
      5 (H05)

<400> SEQUENCE: 9

Glu Val Gln Leu Leu Glu Ser Gly Gly Gly Leu Val Gln Pro Gly Gly
1                5                10                15

Ser Leu Arg Leu Ser Cys Ala Ala Ser Gly Phe Thr Phe Ser Asn Tyr
                  20                25                30

Gly Met Ser Trp Val Arg Gln Ala Pro Gly Lys Gly Leu Glu Trp Val
              35                40                45

Ser Thr Ile Ser Asn Ser Gly Arg Tyr Thr Tyr Phe Pro Asp Ser Val
     50                55                60

Lys Gly Arg Phe Thr Ile Ser Arg Asp Asn Ser Lys Asn Thr Leu Tyr
65                70                75                80

Leu Gln Met Asn Ser Leu Arg Ala Glu Asp Thr Ala Val Tyr Tyr Cys
                  85                90                95

Ala Lys His Leu Asp Tyr Ala Asn Tyr Asp Ala Met Asp Tyr Trp Gly
              100                105                110

Gln Gly Thr Leu Val Thr Val Ser Ser
          115                120

<210> SEQ ID NO 10
<211> LENGTH: 121
<212> TYPE: PRT
<213> ORGANISM: Artificial Sequence
<220> FEATURE:
<223> OTHER INFORMATION: Humanized antibody heavy chain variable region
      6 (H06)

<400> SEQUENCE: 10

Glu Val Gln Leu Val Glu Ser Gly Gly Gly Leu Val Lys Pro Gly Gly
1                5                10                15

Ser Leu Arg Leu Ser Cys Ala Ala Ser Gly Phe Thr Phe Ser Asn Tyr
                  20                25                30

Gly Met Ser Trp Val Arg Gln Ala Pro Gly Lys Gly Leu Glu Trp Val
              35                40                45

Ser Thr Ile Ser Asn Ser Gly Arg Tyr Thr Tyr Phe Pro Asp Ser Val
     50                55                60

Lys Gly Arg Phe Thr Ile Ser Arg Asp Asn Ala Lys Asn Ser Leu Tyr
65                70                75                80

Leu Gln Met Asn Ser Leu Arg Ala Glu Asp Thr Ala Val Tyr Tyr Cys
                  85                90                95

Ala Arg His Leu Asp Tyr Ala Asn Tyr Asp Ala Met Asp Tyr Trp Gly
```

-continued

```
                100              105              110

Gln Gly Thr Leu Val Thr Val Ser Ser
      115              120

<210> SEQ ID NO 11
<211> LENGTH: 111
<212> TYPE: PRT
<213> ORGANISM: Artificial Sequence
<220> FEATURE:
<223> OTHER INFORMATION: Humanized antibody light chain variable region
      5 (L05)

<400> SEQUENCE: 11

Asp Ile Gln Met Thr Gln Ser Pro Ser Ser Leu Ala Val Ser Leu Gly
1               5                   10                  15

Asp Arg Val Thr Ile Thr Cys Arg Ala Ser Lys Ser Val Thr Thr Ser
            20                  25                  30

Asp Phe Ser Tyr Met His Trp Tyr Gln Gln Lys Pro Gly Leu Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln His Ser Arg
                85                  90                  95

Glu Phe Pro Trp Thr Phe Gly Gln Gly Thr Lys Val Glu Val Lys
            100              105              110

<210> SEQ ID NO 12
<211> LENGTH: 111
<212> TYPE: PRT
<213> ORGANISM: Artificial Sequence
<220> FEATURE:
<223> OTHER INFORMATION: Humanized antibody light chain variable region
      6 (L06)

<400> SEQUENCE: 12

Asp Ile Val Met Thr Gln Thr Pro Leu Ser Ser Pro Val Thr Leu Gly
1               5                   10                  15

Gln Pro Ala Ser Ile Ser Cys Arg Ala Ser Lys Ser Val Thr Thr Ser
            20                  25                  30

Asp Phe Ser Tyr Met His Trp Leu Gln Gln Arg Pro Gly Gln Pro Pro
        35                  40                  45

Arg Leu Leu Ile Tyr Leu Ala Ser Asn Leu Glu Ser Gly Val Pro Asp
    50                  55                  60

Arg Phe Ser Gly Ser Gly Ala Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Glu Phe Pro Trp Thr Phe Gly Gln Gly Thr Lys Val Glu Ile Lys
            100              105              110

<210> SEQ ID NO 13
<211> LENGTH: 111
<212> TYPE: PRT
<213> ORGANISM: Artificial Sequence
<220> FEATURE:
<223> OTHER INFORMATION: Humanized antibody light chain variable region
      7 (L07)

<400> SEQUENCE: 13
```

```
Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Thr Thr Ser
            20                  25                  30

Asp Phe Ser Tyr Met His Trp Tyr Leu Gln Lys Pro Gly Gln Pro Pro
        35                  40                  45

Gln Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Glu Phe Pro Trp Thr Phe Gly Gln Gly Thr Lys Val Glu Ile Lys
            100                 105                 110
```

<210> SEQ ID NO 14
<211> LENGTH: 121
<212> TYPE: PRT
<213> ORGANISM: Artificial Sequence
<220> FEATURE:
<223> OTHER INFORMATION: Chimeric antibody heavy chain variable region 7
      (H07)

<400> SEQUENCE: 14

```
Glu Val Lys Leu Val Glu Ser Gly Gly Val Leu Val Lys Ser Gly Gly
1               5                   10                  15

Ser Leu Lys Leu Ser Cys Ala Val Ser Gly Phe Thr Phe Ser Asn Tyr
            20                  25                  30

Gly Met Ser Trp Val Arg Gln Thr Pro Glu Lys Arg Leu Glu Trp Val
        35                  40                  45

Ala Thr Ile Ser Asn Ser Gly Arg Tyr Thr Tyr Phe Pro Asp Ser Val
    50                  55                  60

Lys Gly Pro Phe Ala Ile Ser Arg Asp Asn Ala Lys Asn Asn Leu Tyr
65                  70                  75                  80

Leu Gln Met Ser Ser Leu Arg Ser Ala Asp Thr Ala Leu Tyr Tyr Cys
                85                  90                  95

Thr Arg His Leu Asp Tyr Ala Asn Tyr Asp Ala Met Asp Tyr Trp Gly
            100                 105                 110

Gln Gly Thr Ser Val Thr Val Ser Ser
        115                 120
```

<210> SEQ ID NO 15
<211> LENGTH: 111
<212> TYPE: PRT
<213> ORGANISM: Artificial Sequence
<220> FEATURE:
<223> OTHER INFORMATION: Chimeric antibody light chain variable region 8
      (L08)

<400> SEQUENCE: 15

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Thr Thr Ser
            20                  25                  30

Asp Phe Ser Tyr Met His Trp Tyr Gln Gln Lys Pro Gly Gln Pro Pro
        35                  40                  45

Lys Leu Leu Leu Tyr Leu Ala Ser Asn Leu Glu Ser Gly Val Pro Asp
    50                  55                  60
```

-continued

```
Arg Phe Ser Gly Ser Gly Ser Gly Tyr Asp Phe Tyr Leu Asn Ile His
65              70              75                      80

Pro Val Glu Glu Glu Asp Ala Ala Thr Tyr Tyr Cys Gln His Ser Arg
                85              90                      95

Glu Phe Pro Trp Thr Phe Gly Gly Gly Thr Lys Leu Glu Ile Lys
            100             105             110
```

HUMANIZED ANTIBODY AND METHOD FOR USING THE SAME

CROSS REFERENCE TO RELATED APPLICATIONS

This application is a national stage application of International patent application PCT/JP202/039015, filed Oct. 16, 2020, which claims the benefits of priority to Japanese application 2019-191560, filed Oct. 18, 2019. The entire contents of both applications are incorporated herein in their entireties.

SEQUENCE LISTING

The instant application contains a Sequence Listing submitted via patent Center and is hereby incorporated by reference in its entirety. The ASCII file, created on Aug. 12, 2021, is named 538562US_SL.txt, and is 287 bytes in size.

TECHNICAL FIELD

The present invention relates to a humanized antibody that specifically binds to mucin subtype 5AC (MUC5AC) or an antigen-binding fragment thereof, and a method of use thereof.

BACKGROUND ART

Mucin is the main component of mucus secreted from epithelial cell and the like of animal and is a glycoprotein containing a large amount of sugar with a molecular weight of 1-10 million. Mucin includes secretory mucin produced by epithelial cell and the like and membrane-bound mucin that has a hydrophobic transmembrane site and exists while being bound to the cell membrane. The core proteins of mucin are collectively called MUC, and it is known that there are at least 20 types of genes encoding core proteins. One of them, MUC5AC, belongs to secretory mucin.

MUC5AC is expressed in the stomach and trachea in normal tissues, and overexpression in pancreatic cancer has been reported. Overexpression has also been reported in thyroid cancer, liver cancer, colorectal cancer, gastric cancer, urothelial cancer, breast cancer, cervical cancer, ovarian cancer, endometrial cancer, and bile duct cancer. As antibodies to MUC5AC, a mouse antibody prepared using, as an antigen, a pancreatic cancer mucin fraction purified from xenograft of human pancreatic cancer cell line SW1990, and chimeric antibodies (patent documents 1, 2, non-patent documents 1, 2) and humanized antibody (patent document 3) produced based thereon have been reported.

In recent years, antibody-drug complexes in which a drug having an antitumor effect is conjugated to an antibody having a targeting ability to cancer cells have been actively developed. For example, when use of an antibody as a delivery tool for an antibody-drug complex is assumed, since the antibody needs to be further subjected to a production step (for example, conjugating step), denaturation and aggregation of the antibody during the production step is feared. Therefore, antibodies used in production are required to have more stable properties as antibody than general antibody drugs. From other aspect, when use of an antibody as a delivery tool for an antibody-drug complex is assumed, since distribution of drugs with extremely high cell-killing effects in normal tissues leads to enormous side effects, antibodies used for antibody-drug complex are required to have more stable physical properties as antibody and higher accumulation in tumor tissues than general antibody drugs.

The chimeric antibodies disclosed in non-patent documents 1 and 2 have been confirmed to show tumor accumulation in vivo and also in patients with pancreatic cancer. Since accumulation in the liver and kidney has also been observed, application to pharmaceutical products requires further improvement in the tumor accumulation. Non-patent documents 1, 2 do not disclose any information about the physical properties (denaturation, aggregation) of the antibody.

Furthermore, various physical properties of chimeric antibodies disclosed in non-patent documents 1, 2 were evaluated. As a result, it was clarified that antibodies are easily denatured and aggregated when heated (low denaturation midpoint temperature and low aggregation start temperature) and practicability is low when use thereof as, for example, a delivery tool for an antibody-drug complex is assumed. Needless to say, when an antibody is used in a subsequent production step (for example, conjugating step), it is better to use an antibody having as good physical properties as possible (an antibody that does not easily cause denaturation or aggregation).

Patent document 3 discloses a humanized antibody; however, it focuses on obtaining a humanized antibody with high binding activity to MUC5AC, and does not disclose or suggest stability of the antibody. Furthermore, various physical properties of the humanized antibody disclosed in patent document 3 were evaluated. As a result, it was clarified that antibodies are easily aggregated when heated (aggregation start temperature is low) and practicability is low when use thereof as, for example, a delivery tool for an antibody-drug complex is assumed. It is desirable to avoid denaturation and aggregation of antibody as much as possible because a risk leading to a decrease in the efficacy of a compound and the occurrence of side effects is expected. The below-mentioned denaturation midpoint temperature and aggregation start temperature are known to also correlate with long-term stability in refrigeration and the like, and the development of an antibody with good physical properties that does not easily cause denaturation or aggregation of the antibody is desired from the aspect of stability not only during the production step but also during storage.

DOCUMENT LIST

Patent Documents patent document 1: JP-A-H7-203974
patent document 2: JP-A-H11-5749
patent document 3: WO 2013/157102

Non-Patent Documents non-patent document 1: Japanese Journal of Clinical Medicine vol. 64 extra issue 1, 2006, p274-278
non-patent document 2: Japanese Journal of Cancer Research, 90, 1179-1186, 1999

SUMMARY OF INVENTION

Technical Problem

Accordingly, the problem of the present invention is to provide a humanized antibody or an antigen-binding fragment thereof having stable physical property, superior in tumor accumulation, and capable of binding to mucin subtype 5AC. More specifically, a humanized antibody or an antigen-binding fragment thereof that does not easily cause denaturation or aggregation when heated and is capable of binding to mucin subtype 5AC, and also, a humanized antibody or an antigen-binding fragment thereof that shows higher accumulation in tumor tissue than in normal tissue and is capable of binding to mucin subtype 5AC.

Solution to Problem

The present inventors have conducted intensive studies in an attempt to solve the problems and found that the problem can be solved by the following means.

That is, the present invention provides the following.

[1] A humanized antibody capable of binding to mucin subtype 5AC, and comprising or consisting of a heavy chain variable region (1) the amino acid sequence shown in SEQ ID NO: 1, an amino acid sequence having not less than 90% or not less than 951 sequence identity with the amino acid sequence shown in SEQ ID NO: 1, or an amino acid sequence shown in SEQ ID NO: 1 wherein not more than 10 or not more than 5 amino acids are deleted, substituted or added, (2) the amino acid sequence shown in SEQ ID NO: 2, an amino acid sequence having not less than 90% or not less than 95% sequence identity with the amino acid sequence shown in SEQ ID NO: 2, or an amino acid sequence shown in SEQ ID NO: 2 wherein not more than 10 or not more than 5 amino acids are deleted, substituted or added, (3) the amino acid sequence shown in SEQ ID NO: 3, an amino acid sequence having not less than 90% or not less than 95% sequence identity with the amino acid sequence shown in SEQ ID NO: 3, or an amino acid sequence shown in SEQ ID NO: 3 wherein not more than 10 or not more than 5 amino acids are deleted, substituted or added, or (4) the amino acid sequence shown in SEQ ID NO: 4, an amino acid sequence having not less than 90% or not less than 95% sequence identity with the amino acid sequence shown in SEQ ID NO: 4, or an amino acid sequence shown in SEQ ID NO: 4 wherein not more than 10 or not more than 5 amino acids are deleted, substituted or added, and a light chain variable region consisting of (5) the amino acid sequence shown in SEQ ID NO: 5, an amino acid sequence having not less than 90% or not less than 95% sequence identity with the amino acid sequence shown in SEQ ID NO: 5, or an amino acid sequence shown in SEQ ID NO: 5 wherein not more than 10 or not more than 5 amino acids are deleted, substituted or added, (6) the amino acid sequence shown in SEQ ID NO: 6, an amino acid a sequence having not less than 90% or not less than 95% sequence identity with the amino acid sequence shown in SEQ ID NO: 6, or an amino acid sequence shown in SEQ ID NO: 6 wherein not more than 10 or not more than 5 amino acids axe deleted, substituted or added, (7) the amino acid sequence shown in SEQ ID NO: 7, an amino acid a sequence having not less than 90% or not less than 95% sequence identity with the amino acid sequence shown in SEQ ID NO: 7, or an amino acid sequence shown in SEQ ID NO: 7 wherein not more than 10 or not more than 5 amino acids are deleted, substituted or added, or (8) the amino acid sequence shown in SEQ ID NO: 8, an amino acid sequence having not less than 90% or not less than 95% sequence identity with the amino acid sequence shown in SEQ ID NO: 8, or an amino acid sequence shown in SEQ ID NO: 8 wherein not more than 10 or not more than 5 amino acids are deleted, substituted or added, or an antigen-binding fragment thereof.

[2] The humanized antibody, or an antigen-binding fragment thereof of [1], wherein the heavy chain variable region consists (1) the amino acid sequence shown in SEQ ID NO: 1, an amino acid sequence having not less than 90% or not less than 95% sequence identity with the amino acid sequence shown in SEQ ID NO: 1, or an amino acid sequence shown in SEQ ID NO: 1 wherein not more than 10 or not more than 5 amino acids are deleted, substituted or added, (3) the amino acid sequence shown in SEQ ID NO: 3, an amino acid sequence having not less than 90% or not less than 95% sequence s identity with the amino acid sequence shown in SEQ ID NO: 3, or an amino acid sequence shown in SEQ ID NO: 3 wherein not more than 10 or not more than 5 amino acids are deleted, substituted or added, or (4) the amino acid sequence shown in SEQ ID NO: 4, an amino acid sequence having not less than 90% E or not less than 95% sequence identity with the amino acid sequence shown in SEQ ID NO: 4, or an amino acid sequence shown in SEQ ID NO: 4 wherein not more than 10 or not more than 5 amino acids are deleted, substituted or added.

[3] The humanized antibody, or an antigen-binding fragment thereof of [1] or [2], comprising or consisting of (1) a heavy chain variable region consisting of the amino acid sequence shown in SEQ ID NO: 1, an amino acid sequence having not less than 90N or not less than 95% sequence identity with the amino acid sequence shown in SEQ ID NO: 1, or an amino acid sequence shown in SEQ ID NO: 1 wherein not more than 10 or not more than 5 amino acids axe deleted, substituted or added, and (7) a light chain variable region consisting of the amino acid a sequence shown in SEQ ID NO: 7, an amino acid sequence having not less than 90% or not less than 95% sequence identity with the amino acid sequence shown in SEQ ID NO: 7, or an amino acid sequence shown in SEQ ID NO: 7 wherein not more than 10 or not more than 5 amino acids are deleted, substituted or added.

[4] The humanized antibody, or an antigen-binding fragment thereof of [1] or [2], comprising or consisting of
a heavy chain variable region consisting of the amino acid sequence shown in SEQ ID NO: 1, and a light chain variable region consisting of the amino acid sequence shown in SEQ ID NO: 5.

[5] The humanized antibody, or an antigen-binding fragment thereof of [1] or [2], comprising or consisting of
a heavy chain variable region consisting of the amino acid sequence shown in SEQ ID NO: 1, and a light chain variable region consisting of the amino acid sequence shown in SEQ ID NO: 6.

[6] The humanized antibody, or an antigen-binding fragment thereof of any one of [1] to [3], comprising or consisting of a heavy chain variable region consisting of the amino acid sequence shown in SEQ ID NO: 1, and a light chain variable region consisting of the amino acid sequence shown in SEQ ID NO: 7.

[7] The humanized antibody, or an antigen-binding fragment thereof of [1] or [2], comprising or consisting of
a heavy chain variable region consisting of the amino acid sequence shown in SEQ ID NO: 1, and a light chain variable region consisting of the amino acid sequence shown in SEQ ID NO: 8.

[8] The humanized antibody, or an antigen-binding fragment thereof of [1] or [2], comprising or consisting of
a heavy chain variable region consisting of the amino acid sequence shown in SEQ ID NO: 3, and a light chain variable region consisting of the amino acid sequence shown in SEQ ID NO: 5.

[9] The humanized antibody, or an antigen-binding fragment thereof of [1] or [2], comprising or consisting of
a heavy chain variable region consisting of the amino acid sequence shown in SEQ ID NO: 3, and a light chain variable region consisting of the amino acid sequence shown in SEQ ID NO: 6.

[10] The humanized antibody, or an antigen-binding fragment thereof of [1] or [2], comprising or consisting of
a heavy chain variable region consisting of the amino acid sequence shown in SEQ ID NO: 3, and a light chain variable region consisting of the amino acid sequence shown in SEQ ID NO: 7.

[11] The humanized antibody, or an antigen-binding fragment thereof of [1] or [2], comprising or consisting of
a heavy chain variable region consisting of the amino acid sequence shown in SEQ ID NO: 3, and a light chain variable region consisting of the amino acid sequence shown in SEQ ID NO: 8.

[12] The humanized antibody, or an antigen-binding fragment thereof of [1] or [2], comprising or consisting of
a heavy chain variable region consisting of the amino acid sequence shown in SEQ ID NO: 4, and a light chain variable region consisting of the amino acid sequence shown in SEQ ID NO: 5.

[13] The humanized antibody, or an antigen-binding fragment thereof of [1] or [2], comprising or consisting of
a heavy chain variable region consisting of the amino acid sequence shown in SEQ ID NO: 4, and a light chain variable region consisting of the amino acid sequence shown in SEQ ID NO: 6.

[14] The humanized antibody, or an antigen-binding fragment thereof of [1] or [2], comprising or consisting of
a heavy chain variable region consisting of the amino acid sequence shown in SEQ ID NO: 4, and a light chain variable region consisting of the amino acid sequence shown in SEQ ID NO: 7.

[15] The humanized antibody, or an antigen-binding fragment thereof of [1] or [2], comprising or consisting of
a heavy chain variable region consisting of the amino acid sequence shown in SEQ ID NO: 4, and a light chain variable region a consisting of the amino acid sequence shown in SEQ ID NO: 8.

[16] The humanized antibody, or an antigen-binding fragment thereof of any one of [1] to [15], wherein the antibody or antigen-binding fragment is an isolated antibody or an isolated antigen-binding fragment.

[17] The humanized antibody, or an antigen-binding fragment thereof of any one of [1] to [16], wherein the antibody is a polyclonal antibody or a monoclonal antibody.

[18] The humanized antibody of any one of [1] to [17], wherein the antibody has a most frequent particle size (Pk1

Mode Dia.) of not more than 20 nm, not more than 15 nm, not more than 12 nm, not more than 11 nm or not more than 10 nm.

[19] The humanized antibody of any one of [1] to [18], wherein the antibody has a denaturation midpoint temperature (Tm1) of not less than 50° C., not less than 55° C., not less than 56° C., not less than 57° C., not less than 58° C., not less than 59° C. or not less than 60'C.

[20] The humanized antibody of any one of [1] to [19], wherein the antibody has an aggregation start temperature (Tagg) of not less than 50° C., not less than 55° C., not less than 60° C., not less than 61° C., not less than 62° C., not less than 63° C., not less than 64° C. or not less than 65° C.

[21] The humanized antibody of any one of [1] to [20], having an in vitro binding activity to mucin subtype 5AC comparable to or greater than that of a chimeric antibody.

[22] The humanized antibody of any one of [1] to [21], wherein accumulation thereof in a tumor tissue expressing mucin subtype 5AC is not less than 10 times, not less than 11 times, not less than 12 times, not less than 13 times, not less than 14 times, not less than times, not less than 16 times, not less than 17 times, not less than 18 times, not less than 19 times or not less than 20 times that in a liver tissue 7 days after administration of the antibody.

[23] The humanized antibody of any one of [1] to [22], wherein accumulation thereof in a tumor tissue expressing mucin subtype 5AC is not less than 10 times, not less than 11 times, not less than 12 times, not less than 13 times, not less than 14 times, not less than 15 times, not less than 16 times or not less than 17 times that in a kidney tissue 7 days after administration of the antibody.

(24) A composition comprising the humanized antibody of any one of [1] to [23], or an antigen-binding fragment thereof.

[25] A pharmaceutical composition comprising the humanized antibody of any one of [1] to [23], or an antigen-binding fragment thereof, and a pharmaceutically acceptable carrier.

(26) A pharmaceutical composition for treating a cancer overexpressing mucin subtype 5AC, comprising the humanized antibody of any one of [1] to [23], or an antigen-binding fragment thereof, and a pharmaceutically acceptable carrier.

[27] The pharmaceutical composition of [26], wherein the cancer is pancreatic cancer, thyroid cancer, liver cancer, colorectal cancer, gastric cancer, urothelial cancer, breast cancer, cervical cancer, ovarian cancer, endometrial carcinoma, or bile duct cancer.

[28] The pharmaceutical composition of [27], wherein the cancer is pancreatic cancer.

[29] An antibody-drug conjugate comprising the humanized antibody of any one of [1] to [23], or an antigen-binding fragment thereof, and a drug used for diagnosis and/or treatment which is conjugated thereto.

[30] The antibody-drug conjugate of [29], wherein the drug is a toxin, a fluorescence labeling substance, a nucleic acid medicament, a viral vector, a nanoparticle, a low-molecule drug or a cytokine.

[31] The antibody-drug conjugate of [29] or [30], wherein the humanized antibody or an antigen-binding fragment, and the drug are connected by a linker.

[32] The antibody-drug conjugate of [31], wherein the linker is one to several linkers selected from the group consisting of a PEG linker, a maleimide linker, a PASylated linker, an HESylated linker, a bis(sulfosuccinimidyl)suberate linker, a nucleic acid linker, a peptide linker, a silane linker, a polysaccharide linker, a linker that is a temperature-sensitive or irradiation (IR, near-IR, UV)-sensitive bond, a linker that is a pH-sensitive bond, a hydrolytic linker, and a linker produced by covalent coupling, amide coupling, addition to carbon-carbon multiple bond, Husgene cycloaddition to azidoalkyne, Diels-Alder reaction, disulfide binding, Michael addition, silane coupling, nucleophilic ring-opening reaction of urethane, epoxide, non-aldol carbonyl chemistry, and 1,3-dipolar addition reaction or cycloaddition reaction such as tosylation.

[33] A pharmaceutical composition comprising the antibody-drug conjugate of any one of [29] to [32], and a pharmaceutically acceptable carrier.

[34] A nucleic acid encoding the humanized antibody of any one of [1] to [23].

[35] An expression vector comprising the nucleic acid of [34].

[36] A host cell comprising the expression vector of [35].

[37] A method for producing the humanized antibody of any one of [1] to [23], or an antigen-binding fragment thereof, comprising (1) a step of inserting a nucleic acid encoding the humanized antibody or an antigen-binding fragment thereof into an expression vector, (2) a step of introducing the above-mentioned nucleic acid into a host cell by the expression vector containing the nucleic acid, (3) a step of culturing the host cell containing the expression vector, and (4) a step of isolating the humanized antibody or an antigen-binding fragment thereof from a culture supernatant of the host cell by purifying by chromatography.

[38] Use of the humanized antibody of any one of [1] to [23], or an antigen-binding fragment thereof in producing the composition of [24], the pharmaceutical composition of any one of [25] to [28] and [33], or the antibody-drug conjugate of any one of [29] to [32].

[39] A method for evaluating an expression level of mucin subtype 5AC in a cell or a tissue, comprising (1) a step of obtaining a labeled humanized antibody or an antigen-binding fragment thereof by attaching a label to the humanized antibody of any one of [1] to [23] or an antigen-binding fragment thereof, wherein the label enables detection of the antibody or the antigen-binding fragment, (2) a step of contacting the cell or tissue with the labeled humanized antibody or an antigen-binding fragment thereof, and (3) a step of measuring the amount of the label bound to the cell or tissue, and evaluating based thereon an expression level of u mucin subtype 5AC expressed in the cell or tissue.

[40] A therapeutic agent for a cancer overexpressing mucin subtype 5AC, comprising an effective amount of a pharmaceutical composition comprising the humanized antibody of any one of [1] to [23] or an antigen-binding fragment thereof, or the antibody-drug conjugate of any one of [29] to [32], and a pharmaceutically acceptable carrier.

[41] The therapeutic agent for cancer of [40], wherein the drug decreases the number of cancer cells and/or reduces the size of tumor.

[42] A method for measuring the volume of a cancer overexpressing mucin subtype 5AC in a subject, comprising (1) a step of obtaining a labeled humanized antibody or an antigen-binding fragment thereof by attaching a label to the humanized antibody of any one of [1] to [23] or an antigen-binding fragment thereof, wherein the label enables detection of the antibody or the antigen-binding fragment, (2) a step of contacting a tissue of the subject and a normal tissue with the labeled humanized antibody or an antigen-binding fragment thereof, (3) a step of measuring the amount of the label in the tissue of the subject and the normal tissue, and (4) a step of comparing the amount of the label measured in the tissue of the subject with a standard amount which is the amount of the label measured in the normal tissue, and a step of measuring the volume of a cancerous tissue in a part where the amount measured in the tissue of the subject is larger than the standard amount.

[43] A method for diagnosing whether a subject is affected with a cancer overexpressing mucin subtype 5AC, comprising (1) a step of obtaining a labeled humanized antibody or an antigen-binding fragment thereof by attaching a label to the humanized antibody of any one of [1] to [23] or an antigen-binding fragment thereof, wherein the label enables detection of the antibody or the antigen-binding fragment, (2) a step of contacting a cell or tissue of the subject and a normal cell or tissue with the labeled humanized antibody or an antigen-binding fragment thereof, (3) a step of measuring the amount of the label in the cell or tissue of the subject and the normal tissue, and (4) a step of comparing the amount of the label measured in the cell or tissue of the subject with a standard amount which is the amount of the label measured in the normal cell or tissue and, when the amount measured in the cell or tissue of the subject is significantly larger than the standard amount, diagnosing that the subject is affected with a cancer overexpressing mucin subtype 5AC.

[44] The method of [42] or [43], wherein the contact step is performed in vitro.

[45] A method for measuring a volume of a cancer overexpressing mucin subtype 5AC in a subject, comprising (1) a step of obtaining a labeled humanized antibody or an antigen-binding fragment thereof by attaching a label to the a humanized antibody of any one of [1] to [23] or an antigen-binding fragment thereof, wherein the label enables detection of the antibody or the antibody-binding fragment, (2) a step of detecting the label in a tissue of the subject administered with the labeled humanized antibody or an antigen-m binding fragment thereof, and (3) a step of measuring the volume of a part where accumulation of the labeled humanized antibody or an antigen-binding fragment thereof was found in the above-mentioned step (2).

[46] A method for diagnosing whether a subject is affected with a cancer overexpressing mucin subtype 5AC, comprising (1) a step of obtaining a labeled humanized antibody or an antigen-binding fragment thereof by attaching a label to the humanized antibody of any one of [1] to [23] or an antigen-binding fragment thereof, wherein the label enables detection of the antibody or the antigen-binding fragment, (2) a step of detecting the label in a tissue of the subject administered with the labeled humanized antibody or an antigen-binding fragment thereof, and (3) a step of diagnosing that the subject is affected with a cancer overexpressing mucin subtype 5AC when accumulation of the labeled humanized antibody or an antigen-binding fragment thereof was found in the tissue of the subject in the above-mentioned step (2).

[47] The method of [45] or [46], wherein the detection step is performed in vitro.

[48] A method for treating a cancer overexpressing mucin subtype 5AC, comprising administering an effective amount of a pharmaceutical composition comprising the humanized antibody of any one of [1] to [23] or an antigen-binding fragment thereof and a pharmaceutically acceptable carrier to a subject affected with the cancer.

[49] The method of [48] that decreases the number of cancer cells and/or reduces the size of tumor.

[50] A method for diagnosing whether a subject is affected with a cancer overexpressing mucin subtype 5AC, comprising (1) a step of obtaining a labeled humanized antibody or an antigen-binding fragment thereof by attaching a label to the humanized antibody of any one of [1] to [23] or an antigen-binding fragment thereof, wherein the label enables detection of the antibody or the antigen-binding fragment, (2) a step of collecting a cell or tissue from the subject and a healthy subject, (3) a step of contacting the cell or tissue with the labeled humanized antibody or an antigen-binding fragment thereof, (4) a step of measuring the amount of the label in the cell or tissue, and (5) a step of diagnosing that the subject is affected with a cancer overexpressing mucin subtype 5AC when the amount of the label measured in the cell or tissue collected from the subject is significantly larger than the amount of the label measured in the cell or tissue collected from the healthy subject.

[51] A method for diagnosing whether a subject is affected with a cancer overexpressing mucin subtype 5AC, comprising (1) a step of obtaining a labeled humanized antibody or an antigen-binding fragment thereof by attaching a label to the humanized antibody of any one of [1] to [23] or an antigen-binding fragment thereof, wherein the label enables detection of the antibody or the antigen-binding fragment, (2) a step of administering the labeled humanized antibody or an antigen-binding fragment thereof to the subject, (3) a step of detecting the label in a tissue of the subject, and (4) a step of diagnosing that the subject is affected with a cancer overexpressing mucin subtype 5AC when accumulation of the labeled humanized antibody or an antigen-binding fragment thereof was found in the tissue of the subject in the above-mentioned step (3).

[52] A method for treating a cancer of a subject diagnosed to have been affected with a cancer overexpressing mucin subtype 5AC in the method of [50] or [51], comprising a step of administering an effective amount of a pharmaceutical composition comprising the humanized antibody of any one of [1] to [23] or an antigen-binding fragment thereof and a pharmaceutically acceptable carrier to the subject.

[53] A kit for the treatment and/or diagnosis of a cancer overexpressing mucin subtype 5AC, comprising the humanized antibody of any one of [1] to [23] or an antigen-binding fragment thereof with a label that enables detect-on of the antibody or an antigen-binding antibody fragment thereof.

Advantageous Effects of Invention

The present inventors have conducted intensive studies in an attempt to solve the problems and successfully found a humanized antibody that has the ability to bind to mucin subtype 5AC and is not easily denatured or aggregated even when heated, that is, a humanized antibody that has the above-mentioned binding activity, as well as has a high denaturation midpoint temperature and a high aggregation start temperature, and shows very high accumulation in tumor tissues than in normal tissues, which resulted in the completion of the present invention.

BRIEF DESCRIPTION OF DRAWINGS

FIG. 1 shows the amino acid sequences of the heavy chain variable regions 1-4 (H01-H04) (SEQ ID NOS: 1, 2, 3, and 4, respectively) of the humanized antibody of the present invention.

FIG. 2 shows the amino acid sequences of the light chain variable regions 1-4 (L01-L04) (SEQ ID NOS: 5, 6, 7 and 8, respectively) of the humanized antibody of the present invention.

FIG. 3 shows the amino acid sequences of the heavy chain variable regions 5-6 (H05-H06) SEQ ID NOS: 9 and 10, respectively) and the light chain variable regions 5-7 (L05-L07)) SEQ ID NOS: 11, 12 and 13, respectively) of the humanized antibody of patent document 3.

FIG. 4 shows the amino acid sequences of the heavy chain variable region 7 (H07) (SEQ ID NO: 14) and the light chain variable region 8 (L08)(SEQ ID NO:15) of the chimeric antibody of patent a document 1.

Figure 5:
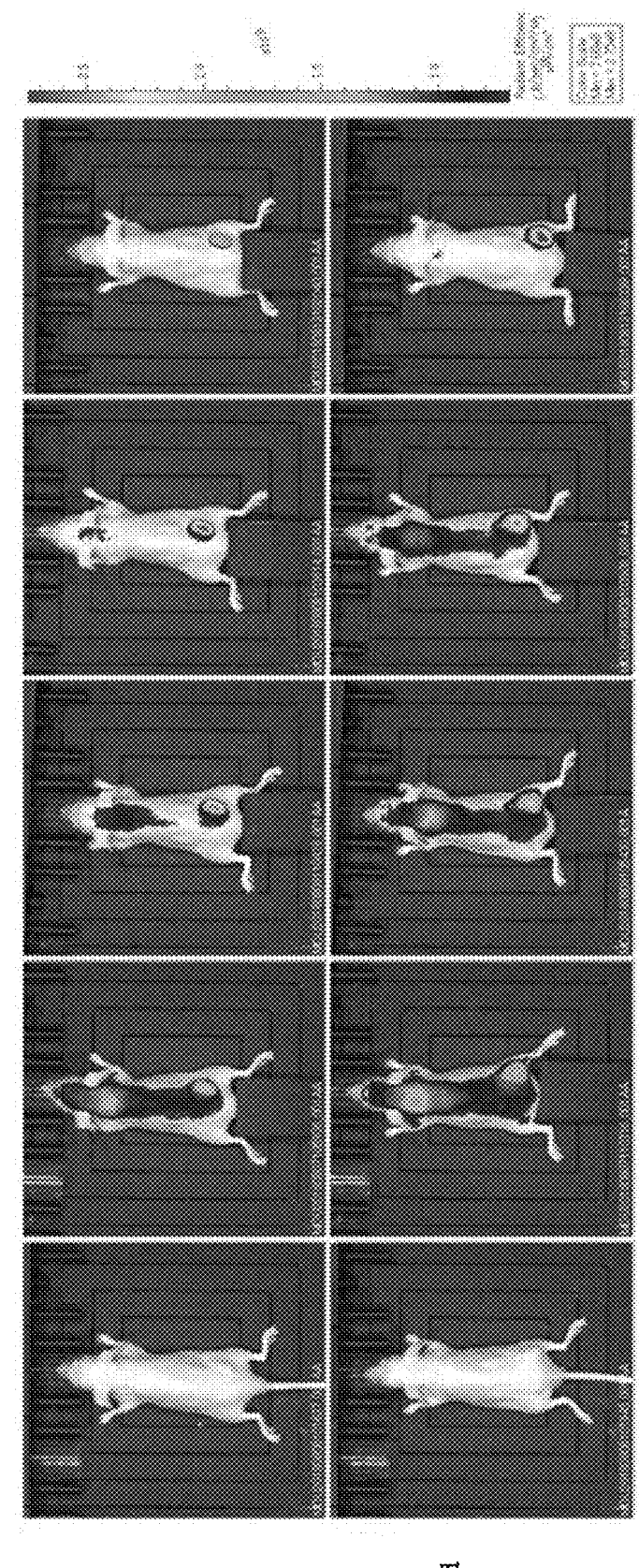
FIG. 5 is a photograph showing the in vivo tumor accumulation of example 3-1 (antibody 3) over time. The upper panel of FIG. 5 is a photograph of a first mouse, and the lower panel is a photograph of a second mouse. Photographs of mice before administration, 1 day after administration, 2 days after administration, 3 days after administration, and 7 days after administration are shown in this order from the left.

DESCRIPTION OF EMBODIMENTS (1) Humanized Antibody of the Present Invention

The present invention provides a humanized antibody having a specific heavy chain variable region and a specific light chain variable region, and capable of binding to mucin subtype 5AC, and an antigen-binding fragment thereof. The humanized antibody of the present invention is characterized in that it has stable physical property and is superior in tumor accumulation. The humanized antibody of the present invention may further have an appropriate heavy chain constant region and an appropriate light chain constant region in addition to a specific heavy chain variable region and a specific light chain variable region.

In the present specification, the "humanized antibody" refers to an antibody having a complementarity determining region (CDR) derived from a non-human, in which at least a part of the heavy chain variable region and/or light chain variable region other than CDR has been modified to be more "human-like", namely, more similar to a human germ line variable sequence. Complementarity determining regions exist in each variable region of the heavy chain and light chain of the antibody, and they are referred to as complementarity determining region 1 (CDR1), complementarity determining region 2 (CDR2), and complementarity determining region 3 (CDR3) from the N-terminal side. A framework region is a region adjacent to a complementarity determining region in a variable region, and they are referred to as framework region 1 (FR1), framework region 2 (FR2), framework region 3 (FR3), and framework region 4 (FR4) from the N-terminal side.

In the present specification, the "antigen-binding fragment" means an antibody fragment consisting of a part of the humanized antibody of the present invention, and having the binding ability to mucin subtype 5AC. The number of amino acids contained in the polypeptide constituting the antigen-binding fragment is not particularly limited as long as it has the binding ability to mucin subtype 5AC.

FIG. 1 shows the amino acid sequence of the heavy chain variable region in the present invention. The heavy chain variable region 1 (H01), heavy chain variable region 2 (H02), heavy chain variable region 3 (L03), and heavy chain variable region 4 (H04) in FIG. 1 respectively correspond to SEQ ID NO: 1-4 in the Sequence Listing attached to the present specification. The underlined part in FIG. 1 is the CDR site.

FIG. 2 shows the amino acid sequence of the light chain variable region in the present invention. The light chain variable region 1 (L01), light chain variable region 2 (L02), light chain variable region 3 (L03), and light chain variable region 4 (L04) in FIG. 2 respectively correspond to SEQ ID NO: 5-8 in the Sequence Listing attached to the present specification. The underlined part in FIG. 2 is the CDR site.

In other words, the heavy chain variable region of the humanized antibody of the present invention consists of the amino acid sequence shown in any one of SEQ ID NO: 1 to SEQ ID NO: 4, and the light chain variable region consists of the amino acid sequence shown in any one of SEQ ID NO: 5 to SEQ ID NO: 8. That is, the humanized antibody of the present invention consists of a combination of the above-mentioned four heavy chain variable regions (H01-H04) and four light chain variable regions (L01-L04).

The four heavy chain variable regions (H01-H04) and four light chain variable regions (L01-L04) of the present invention are obtained by humanizing the variable region of a mucin subtype 5AC-specific antibody based on a chimeric antibody and designing the antibody to improve thermal stability, aggregation property, and tumor accumulation. The CDR site required for binding to the antigen has not been changed. The term "chimeric antibody" in the present specification means a chimeric antibody disclosed in patent document 1 unless otherwise described.

A preferable humanized antibody in the present invention has heavy chain variable region H01, H03, or H04, and any one of L01-L04 as the light chain variable region.

The most preferable humanized antibody in the present invention has heavy chain variable region H01 and light chain variable region L03.

However, the heavy chain variable region of the humanized antibody in the present invention is not limited to those defined by the amino acid sequence shown in SEQ ID NO: 1 to SEQ ID NO: 4 and also includes variants maintaining functions. That is, a mutated heavy chain variable region consisting of an amino acid sequence having not less than 90%, preferably not less than 95%, further preferably not less than 98%, most preferably not less than 99%, sequence identity with the amino acid sequence shown in SEQ ID NO: 1 to SEQ ID NO: 4 is also encompassed in the heavy chain variable region in the present invention as long as it can bind to mucin subtype 5AC when combined with the light chain variable region in the present invention.

In the present specification, the identity of the amino acid sequence refers to the identity of the amino acid sequences between the two proteins of interest, and is shown by the percentage (%) of amino acid residues that match in the optimal alignment of the amino acid sequences prepared using mathematical algorithms known in the pertinent technical field. The identity of an amino acid sequence can be determined by visual inspection and mathematical calculation, and can be calculated using a homology search program (e.g., BLAST, FASTA) or sequence alignment program (e.g., ClustalW) known to those skilled in the art, or genetic information processing software (e.g., GENETYX [registered trade mark]), and the like. To be specific, the identity of the amino acid sequence in the present specification can be determined using systematic analysis program (ClustalW clustalw.ddbj.nig.ac.jp) published on the website of DDBJ (DNA DataBank of Japan) by the initial setting conditions (Version2.1, Alignment type:slow, DNA Weight Matrix: Gonnet, GAP OPEN: 10, GAP EXTENSION: 0.1).

In addition, as the heavy chain variable region of the humanized antibody in the present invention, a mutated heavy chain variable region consisting of the amino acid sequence shown in SEQ ID NO: 1 to SEQ ID NO: 4, wherein not more than 10, preferably not more than 8, further preferably not more than 5, most preferably not more than 3, amino acids are deleted, substituted, or added, is also encompassed in the heavy chain variable region in the present invention as long as it can bind to mucin subtype 5AC when combined with the light chain variable region in the present invention.

The light chain variable region of the humanized antibody in the present invention is not limited to the amino acid sequence shown in SEQ ID NO: 5 to SEQ ID NO: 8 and also includes variants maintaining functions. That is, a mutated light chain variable region consisting of an amino acid sequence having not less than 90%, preferably not less than 95%, further preferably not less than 98%, most preferably not less than 99%, sequence identity with the amino acid sequence shown in SEQ ID NO: 5 to SEQ ID NO: 8 is also encompassed in the light chain variable region in the present invention as long as it can bind to mucin subtype 5AC when combined with the heavy chain variable region in the present invention.

In addition, as the light chain variable region of the humanized antibody in the present invention, a mutated light chain variable region consisting of the amino acid sequence shown in SEQ ID NO: 5 to SEQ ID NO: 8, wherein not more than 10, preferably not more than 8, further preferably not more than 5, most preferably not more than 3, amino acids are deleted, substituted, or added, is also encompassed in the light chain variable region in the present invention as long as it can bind to mucin subtype 5AC when combined with the heavy chain variable region in the present invention.

The humanized antibody or antigen-binding fragment of the present invention may be an isolated antibody or an isolated antigen-binding fragment. That is, the humanized antibody of the present invention is, for example, isolated from a culture supernatant of a host cell introduced with a nucleic acid encoding the humanized antibody or an antigen-binding fragment of the present invention. Such nucleic acid and host cell are described in detail later.

In addition, the humanized antibody of the present invention may be a polyclonal antibody or a monoclonal antibody.

Furthermore, the humanized antibody of the present invention has stable physical property and does not aggregate easily. The most frequent particle size of the humanized antibody of the present invention is small and specifically not more than 20 nm, not more than 15 nm, not more than 12 nm, not more than 11 nm or not more than 10 nm. When aggregation of antibody occurs, many antibodies having a particle size exceeding 100 nm are detected. In the present specification, the most frequent particle size refers to the particle size most frequently detected when the particle size distribution of the humanized antibody of the present invention is measured.

One of the characteristics of the humanized antibody of the present invention is that it does not easily denatured when heat is applied. To be specific, the denaturation midpoint temperature of the humanized antibody of the present invention is not less than 50° C., not less than 55° C., not less than 56° C., not less than 57° C., not less than 58° C., not less than 59° C. or not less than 60° C. When the humanized antibody of the present invention is heated and the antibody is denatured, the peak center of gravity of the fluorescence spectrum of the amino acids inherently present in the antibody shifts. The denaturation midpoint temperature in the present specification refers to the temperature at the midpoint of the shift of the peak center of gravity (the temperature at which the normal state and the degenerated state reach 1:1).

One of the characteristics of the humanized antibody of the present invention is that it does not easily aggregate when heat is applied. To be specific, the aggregation start temperature (Tagg) of the humanized antibody of the present invention is not less than a 50° C., not less than 55° C., not less than 60° C., not less than 61° C., not less than 62° C., not less than 63° C., not less than 64° C. or not less than 65° C. When the humanized antibody of the present invention is heated and the antibody aggregates, the scattering intensity when static light scattering is measured becomes high. In the present specification, the aggregation start temperature refers to the temperature at which the scattered light starts to become stronger. In the following Example, the scattered light was measured at 266 nm.

Furthermore, the humanized antibody of the present invention characteristically has high in vitro binding activity to mucin subtype 5AC. To be specific, the in vitro binding activity of the humanized antibody of the present invention to mucin subtype 5AC is comparable to or not less than that of the chimeric antibody disclosed in patent document 1. As used herein, "comparable to" can mean the same and can also mean a difference of about not more than 2.0 times, not more than 1.9 times, not more than 1.8 times, not more than 1.7 times, not more than 1.6 times, not more than 1.5 times, not more than 1.4 times, not more than 1.3 times, not more than 1.2 times or not more than 1.1 times, or not less than 1.0 times, not less than 0.9 times, not less than 0.8 times, not less than 0.7 times, not less than 0.6 times or not less than 0.5 times.

Furthermore, since the humanized antibody of the present invention has high binding activity to mucin subtype 5AC, it shows high accumulation in tumor tissues expressing mucin subtype 5AC in vivo when administered to a living body. In the present specification, "accumulation in tumor tissues expressing mucin subtype 5AC" refers to how many times the humanized antibody of the present invention accumulates in tumor tissue expressing mucin subtype 5AC as compared with normal tissue.

The accumulation in a tumor tissue expressing mucin subtype 5AC is not less than 10 times, not less than 11 times, not less than times, not less than 13 times, not less than 14 times, not less than 15 times, not less than 16 times, not less than 17 times, not less than 18 times, not less than 19 times or not less than 20 times that in a liver tissue 7 days after administration of the humanized antibody of the present invention. The accumulation in a tumor tissue expressing mucin subtype 5AC is not less than 10 times, not less than 11 times, not less than 12 times, not less than 13 times, not less than 14 times, not less than 15 times, not less than 16 times or not less than 17 times that in a kidney tissue 7 days after administration of the humanized antibody of the present invention.

(2) Composition Containing the Humanized Antibody of the Present Invention

The present invention provides a composition containing the humanized antibody of the present invention described in (1) or an antigen-binding fragment thereof. The composition containing the humanized antibody of the present invention is useful for the treatment and/or diagnosis of cancer overexpressing mucin subtype 5AC.

That is, the present invention is a pharmaceutical composition containing the humanized antibody of the present invention, and a pharmaceutically acceptable carrier. The humanized antibody or an antigen-binding fragment thereof of the present invention specifically binds to mucin subtype 5AC, and suppresses proliferation of the cancer cells expressing same. Therefore, the pharmaceutical composition of the present invention is useful for treating a cancer overexpressing mucin subtype 5AC.

Examples of the cancer to be treated by the present invention include pancreatic cancer, thyroid cancer, liver cancer, colorectal cancer, gastric cancer, urothelial cancer, breast cancer, cervical cancer, ovarian cancer, and endometrial carcinoma, and particularly, pancreatic cancer can be treated efficiently.

Examples of the cancer to be treated by the present invention also include bile duct cancer.

There are plural reports stating that mucin subtype 5AC is an antigen carrier for CA19-9 (PLoS ONE (December 2011, Volume 6, Issue 12, e29180, p1-10)). Therefore, examples of the cancer to be treated by the present invention also include biliary tract cancer, uterine cancer, lung cancer, and esophageal cancer overexpressing CA19-9, and these can be treated efficiency.

The dosage form of the pharmaceutical composition of the present invention is not particularly limited and, for example, oral preparations such as tablet, powder, granule, suspension, emulsion, capsule and the like, or parenteral agents such as injection, suppository, external liquid and the like can be prepared. The pharmaceutically acceptable carrier used in the present invention may be one generally used in the pertinent technical field, and can be appropriately selected by those of ordinary skill in the art in consideration of the dosage form and the administration route.

As the pharmaceutically acceptable carrier used in the present invention, for example, excipient, binder, lubricant, surfactant, diluent, preservative, stabilizer, corrigent, moisturizing agent, preservative, antioxidant and the like can be used for oral preparations such as tablet and the like, and a pharmaceutical preparation can be formulated according to a conventional method. At that time, those of ordinary skill in the art can select, for example, appropriate surfactant, diluent, preservative, stabilizer, corrigent, moisturizing agent, preservative, and antioxidant based on the common technical knowledge in the pertinent field.

In the case of parenteral administration, injections are typical. The pharmaceutically acceptable carrier used in the present invention for injections may be, for example, a water-soluble solvent such as physiological saline, Ringer's solution and the like, or a water-insoluble solvent such as vegetable oil or fatty acid ester and the like, and the preparation can be formulated by dissolving therein. At that time, for example, isotonicity agent, solubilizing agent, stabilizer, preservative, suspending agent, emulsifier and the like can be optionally added to prepare the preparation.

(3) Antibody-Drug Conjugate in which a Drug is Connected to the Humanized Antibody of the Present Invention The present invention provides an antibody-drug conjugate in which a drug used for the diagnosis and/or treatment is connected to the humanized antibody or an antigen-binding fragment thereof described in (1). Specific examples of the drug include toxin, fluorescence labeling substance, nucleic acid medicament, viral vector, nanoparticle, low-molecular-weight drug, and cytokine. Since the humanized antibody and an antigen-binding fragment thereof of the present invention binds to mucin subtype 5AC, they can contribute to the diagnosis or treatment of cancer overexpressing mucin subtype 5AC by forming a connected body with a drug.

When the above-mentioned drug is a label capable of detecting the antibody of the present invention, for example, a substance for fluorescent labeling, a connected body of the antibody of the present invention and the label can be used as a tool for detecting mucin subtype 5AC. For example, the antibody of the present invention bound to a substance for fluorescent labeling is administered to a living body, and then an organ overexpressing mucin subtype 5AC can be detected based on the label, thereby contributing to the diagnosis of cancer. Even when it is not, administered to a living body, the expression of mucin subtype 5AC in a tissue or cell collected from the living body can be detected by contacting in vitro the tissue or cell with the antibody of the present invention bound to the substance for fluorescent labeling. A method for diagnosing cancer using the antibody of the present invention is described in detail later.

The substance for fluorescent labeling to be bound to the antibody of the present invention unlimitatively includes, for example, fluorescent protein, fluorescent dye and the like. Specific examples of the fluorescent protein include, but are not limited to, green fluorescent protein, red fluorescent protein, and yellow fluorescent protein. Specific examples of the fluorescence dye include, but are not limited to, fluorescein, rhodamine, Cy dye, Alexa Fluor (registered trademark), HiLyte Fiuor™, phycoerythrin (PE), and allophycocyanin (APC).

When the above-mentioned drug is a therapeutic agent, a drug having the effects of both the therapeutic agent and the humanized antibody of the present invention can be produced by forming a connected body. A synergistic increase of the drug efficacy can be achieved by connecting the humanized antibody of the present invention with, for example, a toxin having an anticancer effect, a nucleic acid drug, a viral vector, nanoparticles, a low-molecular-weight drug, or a cytokine.

The "toxin" used in the present specification is a concept that includes "cytotoxin" or "cytotoxic agent", and refers to any drug that is detrimental to the growth and proliferation of cells and can act to reduce, inhibit or destroy cells or malignant tumors. Specific examples include, but are not limited to, ricin, saporin, diphtheria toxin, Pseudomonas toxin and the like.

The "nucleic acid medicament" used in the present specification is a medicament having a natural nucleotide or a chemically-modified nucleotide as a basic skeleton, and refers to any drug that can act directly on a living body without via gene expression. Specific examples include, but are not limited to, siRNA, miRNA, antisense nucleic acid, decoy nucleic acid, aptamer, and CpG oligonucleotide.

The "viral vector" used in the present specification refers to any vector having the ability to efficiently introduce and express a gene of interest by incorporating a foreign gene into a virus in which the replication and proliferation ability has been deleted by genetic engineering, or a virus maintaining a part of the replication and proliferation ability. Specific examples include, but are not limited to, adenovirus, adeno-associated virus, retrovirus, Lentivirus, Sendai-virus, and simple herpes virus.

The "nanoparticle" used in the present specification refers to any nanometer-sized delivery carrier capable of transporting a medicament to a predetermined cell or tissue. Specific examples include, but are not limited to, liposome, nanomicelle, and PLGA nanoparticle.

The "low-molecular-weight drug" used in the present specification is a concept including "cytotoxic agent", "chemotherapeutic agent", "targeted anticancer agent", and "immunotherapeutic agent", and refers to any drug that can be used to treat cell proliferation disorders such as cancer and the like. Specific examples include, but are not limited to, MMAE, MMAF, DM-1, DM-4, 5-fluorouracil, Doxorubicin, irinotecan, calicheamicin and the like.

The "cytokine" used in the present specification refers to any physiologically active substance that is a low-molecular-weight protein secreted from cells, involved in intercellular interactions, and affects surrounding cells. Specific examples include, but are not limited to, TNF-$\alpha$, interferon-$\alpha$, interferon-$\beta$, interferon-$\gamma$, interleukin-2 and the like.

Furthermore, by blending the antibody-drug conjugate and a pharmaceutically acceptable carrier, a pharmaceutical composition for treating a cancer overexpressing mucin subtype 5AC, or a therapeutic agent for a cancer overexpressing mucin subtype 5AC can be provided. The embodiment of such pharmaceutical composition and therapeutic agent is as described for the pharmaceutical composition in (2). Such pharmaceutical composition or therapeutic agent can reduce the number of cancer cells and/or reduce the size of tumor.

In a preferred embodiment of the present invention, the humanized antibody or antigen-binding fragment and a drug are connected by a linker. The linker to be used here is preferably one capable of connecting the antibody of the present invention to a drug efficiently under mild conditions. Specific examples of the linker that can be used in the present invention include, but are not limited to, the linker; a PEG linker, a maleimide linker, a PASylated linker, an HESylated linker, a bis(sulfosuccinimidyl)suberate linker, a nucleic acid linker, a peptide linker, a silane linker, a polysaccharide linker, a linker that is a temperature-sensitive or irradiation (IR, near-IR, UV)-sensitive bond, a linker that is a pH-sensitive bond, a hydrolytic linker, and a linker produced by covalent coupling, amide coupling, addition to carbon-carbon multiple bond, Husgene cycloaddition to azidoalkyne, Diels-Alder reaction, disulfide binding, Michael addition, silane coupling, nucleophilic ring-opening reaction of urethane, epoxide, non-aldol carbonyl chemistry, and 1,3-dipolar addition reaction or cycloaddition reaction such as tosylation.

(4) Nucleic Acid Encoding the Humanized Antibody of the Present Invention, Vector Containing the Nucleic Acid, Host Cell Containing the Vector The present invention provides a nucleic acid encoding the humanized antibody or an antigen-binding fragment thereof described in (1). Since the amino acid sequences of the heavy chain variable region and the light chain variable region of the humanized antibody of the present invention are disclosed in SEQ ID NO: 1 to SEQ ID NO: 8, those of ordinary skill in the art can obtain a nucleic acid encoding a humanized antibody having the amino acid sequences. When expression of the humanized antibody of the present invention by using a host cell is intended as described later, as the codon of the nucleic acid encoding the sane, one optimized for expression in the host is preferably selected.

The mutated heavy chain variable region described in (1) can be prepared by subjecting the nucleic acid encoding the heavy chain variable region shown in SEQ ID NOs: 1-4 to, for example, site-specific mutagenesis (e.g., Nucleic Acid Research, Vol. 10, No. 20, p. 6487-6500, 1982, the contents of which are incorporated in full herein by reference) which is a well-known technique. The mutated light chain variable region can also be prepared by subjecting the nucleic acid encoding the light chain variable region shown in SEQ ID NOs: 5-8 to, for example, site-specific mutagenesis.

An expression vector incorporating such a nucleic acid can be prepared. The vector can optionally contain, in addition to the nucleic acid encoding the humanized antibody of the present invention, Kozak sequence to improve translation efficiency, a signal sequence that promotes secretion of the humanized antibody of the present invention into the medium when introduced into a host, a promoter sequence, and the like. The vector that can be used in the present invention can be selected from those generally used in the pertinent technical field, and plasmid vectors, particularly pcDNA3.4 used in the following Example, are preferred.

Furthermore, the present invention provides a host cell containing the above-mentioned expression vector. Since the thus-obtained host cell contains a nucleic acid encoding the humanized antibody or an antigen-binding fragment thereof described in (1), it can be used in the method for producing a humanized antibody to be described in the following (5). As a method for introducing a gene into a cell, a method conventionally used in the pertinent technical field, for example, a method known to those skilled in the art such as calcium phosphate method, electroporation method, lipofection method, and DEAE-dextran method can be used. An introduction method using the lipofection method is particularly preferred, as performed in the following Example.

As the host cell used for this purpose, those conventionally used in the pertinent technical field can be used. Examples of such host cell include CHO cell, 293 cell, *Escherichia coli, Pichia* yeast, Sf9 cell and the like. Currently, an expression system kit for expressing the protein of interest is also commercially available. The ExpiCHO System (Thermo Fisher Scientific) used in the following Example is particularly preferred for rapid and reliable expression of the protein of interest.

(5) Production Method of the Humanized Antibody of the Present Invention

The present invention also provides a production method of the humanized antibody or an antigen-binding fragment thereof described in (1). The production method includes inserting the nucleic acid encoding the humanized antibody of the present invention or an antigen-binding fragment thereof described in the above-mentioned (4) into an expression vector, introducing the nucleic acid into a host cell by the expression vector containing a the nucleic acid, culturing the host cell after introduction of the nucleic acid, and obtaining the humanized antibody of the present invention from the culture supernatant thereof by a purification means such as chromatography and the like.

It is convenient and preferable to secrete the humanized antibody or an antigen-binding fragment thereof of the present invention in the culture supernatant by culturing the host cell. Therefore, as described in (4), it is desirable to design the vector and select the host cell so that the host cell will efficiently secrete the antibody of the present invention into the culture supernatant.

The humanized antibody or an antigen-binding fragment thereof of the present invention can be obtained from the culture supernatant by using a purification means such as chromatography, and the like. As the means for chromatography, various means known in the pertinent technical field such as affinity chromatography, ion exchange chromatography, size-exclusion chromatography and the like can be used. Affinity chromatography using the protein A column used in the following Example is particularly preferred.

(6) method for treating cancer

The present invention provides a method for treating cancer by using the humanized antibody or an antigen-binding fragment thereof described in (1), or the antibody-drug conjugate. That is, cancer can be treated by administering an effective amount of a pharmaceutical composition containing the humanized antibody or an antigen-binding fragment thereof of the present invention and a pharmaceutically acceptable carrier to a subject affected with a cancer overexpressing mucin subtype 5AC. Since the humanized antibody or an antigen-binding fragment thereof, or an antibody-drug conjugate of the present invention binds to mucin subtype 5AC and suppresses the proliferation of cancer cells overexpressing mucin subtype 5AC, treatment of the cancer can be expected. The dosage form and the administration route of the pharmaceutical composition to be administered here are as described for the pharmaceutical composition in (2).

Examples of the cancer to be treated by the present invention include pancreatic cancer, thyroid cancer, liver cancer, colorectal cancer, gastric cancer, urothelial cancer, breast cancer, cervical cancer, ovarian cancer, and endometrial carcinoma, and particularly, pancreatic cancer can be treated efficiently.

Examples of the cancer to be treated by the present invention also include bile duct cancer.

There are plural reports stating that mucin subtype 5AC is an antigen carrier for CA19-9 (PLoS ONE (December 2011, Volume 6, Issue 12, e29180, p1-10)). Therefore, examples of the cancer to be treated by the present invention also include biliary tract cancer, uterine cancer, lung cancer, and esophageal cancer overexpressing CA19-9, and these can be treated efficiency.

As used herein, the "subject" is a human, or an animal such as mouse, rat, monkey, guinea pig, chimpanzee, sheep, goat, dog, cat, swine, bovine, horse or the like, preferably a human, but is not particularly limited.

As used herein, the "effective amount" is an amount that can afford useful effects of cancer treatment in a subject. The effective amount to be administered to a subject varies depending on the type of subject, body weight of the subject, dosage form (tablet, injection, etc.) and route (oral administration, parenteral administration, etc.) of administration, severity of cancer, and the like. Physicians and veterinarians can consider these factors and determine the appropriate effective amount.

By treating cancer by administering the humanized antibody or an antigen-binding fragment thereof, or antibody-drug conjugate of the present invention, the number of cancer cells decreases and/or the size of the tumor reduces.

(7) Method for Diagnosing Cancer

The present invention provides a method for diagnosing cancer by using the humanized antibody or an antigen-binding fragment thereof described in (1), or an antibody-drug conjugate.

In one embodiment, to the humanized antibody or an antigen-binding fragment thereof, or an antibody-drug conjugate of the present invention is attached a label enabling detection thereof, cells or tissues are collected from a subject and a healthy subject, the collected cells or tissues are contacted with the labeled humanized antibody of the present invention, the amount of the label in the collected cells or tissues is measured, and the amount of the labeled antibody bound to the cells or tissues collected from the subject is compared with the amount of the labeled antibody bound to the cells or tissues collected from the healthy subject, whereby cancer diagnosis can be performed. When the amount of the label detected in the cell or tissue collected from the subject is larger than the amount of the label detected in the cell or tissue collected from the healthy subject, the subject can be diagnosed to have been affected with a cancer overexpressing mucin subtype 5AC.

As used herein, the "healthy subject" is a healthy individual who is clearly not suffering from cancer, unlike the subject to be diagnosed regarding cancer in the present invention. In such healthy subjects, mucin subtype 5AC is not overexpressed and the subject can be used as a control.

As used herein, the "label" means any that binds to the humanized antibody or an antigen-binding fragment thereof of the present invention and enables detection thereof. Specific examples of the label include a substance for fluorescent labeling.

In another embodiment, to the humanized antibody or an antigen-binding fragment thereof of the present invention is attached a label enabling detection thereof, the cell or tissue of the subject and the cell or tissue of the healthy subject are contacted with the labeled humanized antibody or an antigen-binding fragment thereof of the present invention, the amount of the label in the cell or tissue of the subject and the cell or tissue of the healthy subject is measured, and the amount of the label measured in the cell of the subject or the tissue is compared with the standard amount which is the amount of the label measured in the cell or tissue of the healthy subject. When the amount measured in the tissue or cell of the subject is significantly larger than the standard amount, the subject can be diagnosed to have been affected with a cancer overexpressing mucin subtype 5AC.

As used herein, the "standard amount" is the amount of the label measured in a healthy subject, and shows the total of the expression level of mucin subtype 5AC in non-cancerous individuals and the amount of the label that non-specifically bound to cells or accumulated in tissues. Therefore, when the amount of the label measured in a subject to be diagnosed for cancer is greater than the standard amount, overexpression of mucin subtype 5AC is suggested. In this case, the subject can be diagnosed to have been affected with a cancer. In this method, the contact between the cell or tissue of the subject and the labeled antibody of the present invention can be performed using the cell or tissue acquired from the subject and in an in vitro embodiment. It is also possible to perform the contact between the cell or tissue of the subject and the labeled antibody of the present invention in an in vivo embodiment without taking out the cell or tissue from the subject.

In another embodiment, to the humanized antibody or an antigen-binding fragment thereof of the present invention is attached a label enabling detection thereof, cells or tissues are collected from a subject, the collected cells or tissues are contacted with the labeled humanized antibody of the present invention, the amount of the label in the collected cells or tissues is measured, and the amount of the labeled antibody bound to the cells or tissues collected from the subject is compared with the amount of the labeled antibody bound to the normal cells or tissues, whereby cancer diagnosis can be performed. When the amount of the label detected in the cell or tissue collected from the subject is larger than the amount of the label detected in the normal cell or tissue, the cell or tissue can be diagnosed to have been affected with a cancer overexpressing mucin subtype 5AC.

As used herein, the "normal cell or tissue" refers to a cell or tissue collected from a subject to be diagnosed regarding cancer in the present invention or a healthy subject, and diagnosed in advance as a normal cell or tissue. In such normal cell or tissue, mucin subtype 5AC is not overexpressed and it can be used as a control.

In another embodiment, to the humanized antibody or an antigen-binding fragment thereof of the present invention is attached a label enabling detect-on thereof, the labeled humanized antibody or an antigen-binding fragment thereof is administered to the subject, the label is detected in the tissue of the subject, and accumulation of the labeled antibody is detected, whereby cancer diagnosis can be performed. When the accumulation of the labeled humanized antibody or an antigen-binding fragment thereof is found in the tissue of the subject, the subject is diagnosed to have been affected with a cancer overexpressing mucin subtype 5AC. In this method, the detection of the label in the tissue can be performed using the tissue acquired from the subject and in an in vitro embodiment. It is also possible to perform the detection of the label in the tissue of the subject in an in vivo embodiment without taking out the tissue from the subject.

In another embodiment, to the humanized antibody or an antigen-binding fragment thereof of the present invention is attached a label enabling detection thereof, and the label is detected in the tissue of the subject administered with the labeled humanized antibody or an antigen-binding fragment thereof. When the accumulation of the labeled humanized antibody or an antigen-binding fragment thereof is found in the tissue of the subject, the subject can be diagnosed to have been affected with a cancer.

When a subject is diagnosed as being affected with a cancer overexpressing mucin subtype 5AC by the method described above, the cancer can be treated by the administration of a pharmaceutical composition containing the humanized antibody or an antigen-binding fragment thereof described in (1) and a pharmaceutically acceptable carrier to the subject.

Specific examples of the label here include labeling with a substance for fluorescent labeling, but it is not particularly limited as long as the humanized antibody or an antigen-binding fragment thereof of the present invention can be detected. The binding between the antibody and the label may be performed via the linker described in (3) antibody-drug conjugate.

(8) Method for Measuring Volume of Cancer

The present invention provides a method for measuring a volume of a cancer overexpressing mucin subtype 5AC in a subject by using the humanized antibody or an antigen-binding fragment thereof described in (1). In the present specification, the volume of cancer refers to the volume of the part of the tissue of the subject that is composed of cancerous cells, and excludes the volume of the part composed of normal, non-cancerous cells.

In one embodiment, to the humanized antibody or an antigen-binding fragment thereof of the present invention is attached a label enabling detection thereof, the tissue of the subject and the tissue of the healthy subject are contacted with the labeled humanized antibody or an antigen-binding fragment thereof, and the amount of the label in the tissue of the subject and the tissue of the healthy subject is measured. The amount of the label measured in the tissue of the subject is compared with the standard amount which is the amount of the label measured in the tissue of the healthy subject, and the part where the amount measured in the subject is larger than the standard amount is the cancerous tissue and the volume thereof is measured, whereby the volume of the cancer can be measured.

As used herein, the "standard amount" is the amount of the label measured in a healthy subject, and shows the total of the expression level of mucin subtype 5AC in non-cancerous individuals and the amount of the label that non-specifically bound to cells or accumulated in tissues. Therefore, the part where the amount of the label is higher than the standard amount in the tissue of the subject can be judged to be a cancerous tissue, and the volume of the cancer can be determined by measuring the volume of the part.

In still another embodiment, to the humanized antibody or an antigen-binding fragment thereof of the present invention is attached a label enabling detection thereof, the label is detected m in the tissue of the subject administered with the labeled antibody or an antigen-binding fragment thereof, and the volume of the part where accumulation of the labeled humanized antibody or an antigen-binding fragment thereof is found is measured, whereby the volume of the cancer can be measured.

For the measurement of the volume of cancer, a label such as a substance for fluorescent labeling, and the like is detected as an image in the subject by using a device that can detect the label, and the volume can be calculated from the size of the cancerous tissue in which the label is detected in the image, by using an appropriate calculation formula if necessary. The volume can also be determined by removing the tissue from the sample excised from the subject and directly measuring the volume of the part where the label is detected.

Measuring the volume of cancer in a subject is useful for diagnosing the severity of the cancer and the like in the subject. Furthermore, when the subject is under treatment, measuring the volume of cancer in the subject is useful for determining the effect of the treatment.

While the present invention is described in more detail in the following with reference to Examples, the present invention is not limited to these Examples.

EXAMPLE

While the present invention is described in more concretely in the following by referring to examples and comparison examples, the present invention is not limited thereto. The experimental methods and test methods in the examples and comparison examples are as follows.

Experimental Example 1: Preparation of Various Antibodies

The amino acid sequences of various variable regions with signal sequence added thereto and the amino acid sequences of various constant regions were converted into base sequences in consideration of codon usage suitable for expression in CHO cells. A Kozak sequence was added to the initiation codon site of the signal sequence, and a stop codon was added to the C-terminal side of the constant region. Furthermore, restriction enzyme sites were added to the upstream of the Kozak sequence and the downstream of the stop codon so that they could be introduced into the expression gene transfer site of the mammalian cell expression plasmid (pcDNA3.4). Each DNA fragment designed in this way was produced by chemical synthesis. A DNA fragment containing a variable region and a DNA fragment containing a constant region were ligated by fusion PCR to form a desired H chain and a desired L chain.

The produced various antibody genes were subjected to restriction treatment and then purified. Similarly, a plasmid for transient expression in mammalian cell (pcDNA3.4) was also treated with the same restriction enzyme and then purified. The both fragments were mixed at an appropriate mixing ratio and ligated. The ligation reaction solution was mixed with *Escherichia coli* DH5α competent cells and transformed. Colony PCR, single colony isolation, plasmid extraction from small-scale culture medium, and base sequence determination of the insert portion were performed from the resulting transformant, and a plasmid (*Escherichia coli* clone) in which the designed full-length gene of the antibody was correctly inserted in the intended direction with the sequence as designed was selected. Large-scale culture was performed on the selected *Escherichia coli* clone, and plasmid extraction and purification including an endotoxin removal step were performed. The absorbance of the purified plasmid at 260 nm was measured and the concentration was calculated.

Using ExpiCHO System (Thermo Fisher Scientific), transient expression by CHO cells was performed. From the prepared each H chain expression plasmid and each L chain expression plasmid, one H chain and one L chain were selected to achieve the desired combination, transfected by the lipofection method, cultured, and fed. Culture medium was collected 7-13 days after transfection. Centrifuged and filtered culture supernatant was added to Protein A column and the antibody was purified by conventional affinity column chromatography (washing after adsorption, elution with acidic buffer, neutralization of eluate). The absorbance of the purified antibody at 280 nm was measured and the concentration was calculated.

Antibody 1 to antibody 20 were prepared using the method described above. The antibody numbers assigned to the combination of the heavy chain variable region and the light chain variable region are shown below.

antibody 1: H01L01
antibody 2: H01L02
antibody 3: H01L03
antibody 4: H01L04
antibody 5: H02L01
antibody 6: H02L02
antibody 7: H02L03
antibody 8: H02L04
antibody 9: H03L01
antibody 10: H03L02
antibody 11: H03L03
antibody 12: H03L04
antibody 13: H04L01
antibody 14: H04L02
antibody 15: H04L03
antibody 16: H04L04
antibody 17: H05L05
antibody 18: H06L06
antibody 19: H05L07
antibody 20: H07L08

As used herein, H01, H02, H03, and H04 are heavy chain variable regions respectively shown in SEQ ID NO: 1, SEQ ID NO: 2, SEQ ID NO: 3, and SEQ ID NO: 4, and L01, L02, L03, and L04 are light chain variable regions respectively shown in SEQ ID NO: 5, SEQ ID NO: 6, SEO ID NO: 7, and SEQ ID NO: 8. The antibodies of the present invention used in examples 1-1 to 1-16 consist of the combinations of heavy chain constant region 1 and light chain constant region 1, and heavy chain variable regions and light chain variable regions of the above-mentioned antibody 1 to antibody 16.

On the other hand, H05 and H06 are heavy chain variable regions of the humanized antibody disclosed in patent document 3, and L05, L06, and L07 are light chain variable regions of the humanized antibody disclosed in patent document 3. The humanized antibodies of patent document 3 used in comparison examples 1-1 to 1-3 are humanized antibodies of the art that consist of the combinations of heavy chain constant region 1 and light chain constant region 1, and heavy chain variable regions and light chain variable regions of the above-mentioned antibody 17 to antibody 19. The amino acid sequences of H05 and H06 are shown in SEQ ID NO: 9 and SEQ ID NO: 10, and the amino acid sequences of L05, L06, and L07 are shown in SEQ ID NO: 11, SEQ ID NO: 12, and SEQ ID NO: 13. The amino acid sequences of H05 and H06, and amino acid sequences of L05-L07 are shown in FIG. 3.

Furthermore, H07 is a heavy chain variable region of the chimeric antibody disclosed in patent document 1, L08 is a light chain variable region of the chimeric antibody disclosed in patent document 1. The chimeric antibody used in comparison example 1-4 are humanized antibodies of the art that consist of the combinations of heavy chain constant region 1 and light chain constant region 1, and heavy chain variable regions and light chain variable regions of the above-mentioned antibody 20. The amino acid sequence of H07 is shown in SEQ ID NO: 14, and the amino acid sequence L08 is shown in SEQ ID NO: 15. Furthermore, the amino acid sequences of H07 and L08 are shown in FIG. 4.

Test Example 1: Physical Property Evaluation of Antibody

The prepared various antibodies were diluted with 150 mM acetate buffer (pH 4.7) to an antibody concentration of about 1 mg/mL. Since the antibody concentration of comparison example 1-2 was about 0.5 mg/mL, it was used as it was without dilution. These various antibody solutions were determined for the denaturation midpoint temperature, aggregation start temperature, and particle size distribution using UNcle (manufactured by UNchained Labs Co., Ltd.), which is a protein physical property evaluation apparatus. To be specific, for the measurement of denaturation midpoint temperature and aggregation start temperature, various antibodies were heated from around room temperature to 75° C. by 1° C. per min and maintained for 30 sec, and fluorescence spectrum measurement and static light scattering measurement were performed simultaneously over time. From the results of fluorescence spectrum measurement, the midpoint temperature of the shift of the peak center of gravity, that is, the denaturation midpoint temperature, was determined utilizing the phenomenon that the peak center of gravity of the fluorescence spectrum of the amino acid inherent in the antibody shifts when the antibody is denatured. In addition, from the results of static light scattering measurement, the temperature at which the scattered light of 266 nm starts to become stronger, that is, the aggregation start temperature, was obtained utilizing the fact that the scattering intensity becomes stronger when aggregated. The particle size distribution was determined by dynamic light scattering measurement of various antibodies near room temperature.

For antibodies 1-20, the physical property evaluation of various antibodies was performed according to Test Example 1. The results are shown in Table 1. As mentioned above, examples 1-1 to 1-16 are the humanized antibodies of the present invention, comparison examples 1-1 to 1-3 are humanized antibodies of patent document 3, and comparison example 1-4 is chimeric antibody of patent document 1.

TABLE 1

| | | | denaturation midpoint temperature (° C.) | aggregation start temperature (° C.) | most frequent particle size (nm) |
|---|---|---|---|---|---|
| humanized antibody (the present invention) | example 1-1 | antibody 1 | 59.7 | 66.4 | 10.6 |
| | example 1-2 | antibody 2 | 60.2 | 70.0 | 9.9 |
| | example 1-3 | antibody 3 | 59.4 | 67.8 | 9.9 |
| | example 1-4 | antibody 4 | 58.8 | 64.8 | 9.9 |
| | example 1-5 | antibody 5 | 59.6 | 68.1 | 10.7 |
| | example 1-6 | antibody 6 | 59.6 | 66.6 | 9.8 |
| | example 1-7 | antibody 7 | 59.5 | 69.6 | 9.8 |
| | example 1-8 | antibody 8 | 59.3 | 68.5 | 9.9 |
| | example 1-9 | antibody 9 | 59.1 | 65.8 | 9.9 |
| | example 1-10 | antibody 10 | 59.6 | 68.7 | 10.6 |
| | example 1-11 | antibody 11 | 59.1 | 68.2 | 10.7 |
| | example 1-12 | antibody 12 | 59.3 | 65.5 | 11.5 |
| | example 1-13 | antibody 13 | 58.5 | 69.8 | 9.9 |
| | example 1-14 | antibody 14 | 63.5 | 64.3 | 10.6 |
| | example 1-15 | antibody 15 | 59.8 | 67.3 | 10.6 |
| | example 1-16 | antibody 16 | 59.5 | 70.4 | 9.9 |
| humanized antibody (patent document 3) | comparison example 1-1 | antibody 17 | 59.1 | 61.0 | 12.22 |
| | comparison example 1-2 | antibody 18 | 55.5 | 55.9 | 11.76 |
| | comparison example 1-3 | antibody 19 | 60.5 | 61.1 | 10.86 |
| chimeric antibody (patent document 1) | comparison example 1-4 | antibody 20 | 49.5 | 45.4 | 203.15 |

The denaturation midpoint temperature was low and 49.5° C. in the chimeric antibody, and high and 58.5° C.-63.5° C. in the humanized antibody of the present invention. It was clarified that the humanized antibody of the present invention has stable physical property as compared with the chimeric antibody.

The aggregation start temperature was the lowest and 45.4° C. in the chimeric antibody, moderate and about 55.9-61.1° C. in the humanized antibody of patent document 3, and the highest and 64.3° C.-70.4° C. in the humanized antibody of the present invention. It was clarified that the humanized antibody of the present invention has stable physical property as compared with the chimeric antibody and the humanized antibody of patent document 3.

The particle size of the chimeric antibody was about 203 nm, and clear aggregation was found. In the humanized antibody of the present invention, the particle size was about 10 nm, and it was clarified that the humanized antibody is stable and present as monodispersed particles.

From the above results, it was clarified that the humanized antibody of the present invention has more stable physical properties than the chimeric antibody of patent document 1 and the humanized antibody of patent document 3. That is, it is expected that the antibody of the present invention can stably obtain a compound of interest without causing aggregation or the like even when it is subjected to a further production step (for example, a conjugate step of binding to a substance for fluorescent labeling).

Test Example 2: Evaluation of In Vitro Binding Activity

Various antibodies were added to a 96 well plate coated with various antigens, and the plate was left standing for 1 hr at room temperature. The plate was washed, a blocking solution was added, and the mixture was left standing for 30 min at room temperature. The plate was washed, HRP-conjugated anti-human IgG was added, and the mixture was left standing for 1 hr or longer at room temperature. The plate was washed, a color development reagent (Bethyl Laboratories, Inc.) was added, and the degree of color development was measured by a microplate reader (Versa-Max, Molecular Devices, LLC.).

The evaluation results of the binding activity between the antibody and the antigen axe shown in Table 2-Table 4. In Table 2 and Table 3, a tumor mass collected from a cancer-bearing model mouse transplanted with human pancreatic cancer cell line SW1990 was homogenized, and the supernatant (crude extract antigen solution) after centrifugation was used as an antigen. In Table 4, a mucin fraction obtained by isopycnic centrifugation using cesium chloride from the crude extract antigen solution was used as the antigen.

For antibodies 1-20, the in vitro binding activity of various antibodies was evaluated according to Test Example 2. The results are shown in Table 2, Table 3, and Table 4.

Table 2 shows in vitro binding activity ratio of antibodies 2-8 to antibody 1 (Example 2-1), Table 3 shows in vitro binding activity ratio of antibodies 10-16 to antibody 9 (Example 2-9), and Table 4 shows in vitro binding activity ratio of antibodies 3, 4, 8, 16-19 to antibody 20 (comparison example 2-4).

As can be seen from these results, it was clarified that the humanized antibody of the present invention has an in vitro binding activity comparable to that of comparison example 2-4, which is a chimeric antibody of patent document 1. In general, humanization of a chimeric antibody often reduces the binding activity to an antigen. It is surprising that the humanized antibody of the present invention maintained the same level of binding activity as the chimeric antibody. In addition, it was clarified that the humanized antibody of the present invention has an in vitro binding activity comparable to or higher than that of the humanized antibody of patent document 3.

TABLE 2

| humanized | example 2-1 | antibody 1 | 1.00 |
|---|---|---|---|
| antibody | example 2-2 | antibody 2 | 1.03 |
| (the present | example 2-3 | antibody 3 | 0.99 |
| invention) | example 2-4 | antibody 4 | 0.99 |
| | example 2-5 | antibody 5 | 0.60 |
| | example 2-6 | antibody 6 | 0.71 |
| | example 2-7 | antibody 7 | 0.65 |
| | example 2-8 | antibody 8 | 0.72 |

TABLE 3

| humanized | example 2-9 | antibody 9 | 1.00 |
|---|---|---|---|
| antibody | example 2-10 | antibody 10 | 0.96 |
| (the present | example 2-11 | antibody 11 | 1.25 |
| invention) | example 2-12 | antibody 12 | 0.91 |
| | example 2-13 | antibody 13 | 0.90 |
| | example 2-14 | antibody 14 | 1.04 |
| | example 2-15 | antibody 15 | 1.36 |
| | example 2-16 | antibody 16 | 0.88 |

TABLE 4

| humanized | example 2-3 | antibody 3 | 1.56 |
|---|---|---|---|
| antibody | example 2-4 | antibody 4 | 0.97 |
| (the present | example 2-8 | antibody 8 | 0.70 |
| invention | example 2-16 | antibody 16 | 1.09 |
| humanized | comparison | antibody 17 | 0.75 |
| antibody | example 2-1 | | |
| (patent | comparison | antibody 18 | 0.13 |
| document 3) | example 2-2 | | |
| | comparison | antibody 19 | 0.49 |
| | example 2-3 | | |
| chimeric | comparison | antibody 20 | 1.00 |
| antibody | example 2-4 | | |
| (patent | | | |
| document 1) | | | |

Test Example 3 Evaluation of In Vivo Tumor Accumulation

Human pancreatic cancer cell line SW1990 ($1\times10^7$ cells) were subcutaneously administered to Balb/c nude mouse from the flank to the back thereof. When the tumor size reached about 100-200 mm² 13-16 days after transplantation of SW1990, 2 mg/kg of various fluorescent-labeled antibodies were administered from the tail vein of the mouse (n=2). The antibody was fluorescent-labeled using CF (trade mark) Dye SE Protein Labeling Kits (manufactured by Biotium). The tumor volume was calculated from the following calculation formula.

$$\text{tumor volume} = (\text{tumor minor axis}^2 \times \text{tumor major axis})/2$$

(Time-Course Evaluation of Tumor Accumulation)

As time-course evaluation of in vivo tumor accumulation, the fluorescence emitted by the mouse administered with the antibody was photographed using IVIS LuminaIII (Perkin Elmer Inc.) before, one day after, 2 days after, 3 days after, and 7 days after administration of various fluorescent-labeled antibodies.

(Evaluation of Tumor Accumulation at Final Time Point)

In addition, 7 days after administration of various fluorescent-labeled antibodies, the tumor, liver, and kidney were removed and photographed using IVIS Lumina III (Perkin Elmer Inc.). The photographed image data was analyzed using an analysis computer (Living Image software) and numerical data was acquired. The numerical value was calculated as the average brightness $((p/s/cm^2/sr]/[\mu W/cm^2])$ in the area specified in the image.

The tumor accumulation was calculated by the following calculation. The amount of accumulation in tumor here is the average brightness within the tumor area calculated using the above formula, and the accumulation in liver or kidney is the average brightness within the liver area or kidney area calculated using the above formula.

tumor-liver ratio=accumulation in tumor 7 days after administration of fluorescent-labeled antibody/accumulation in liver 7 days after administration of fluorescent-labeled antibody tumor-kidney ratio=accumulation in tumor 7 days after administration of fluorescent-labeled antibody/accumulation in kidney 7 days after administration of fluorescent-labeled antibody For antibodies 3, 4, 8, 9, 10, 16-20, in vivo tumor accumulation of various antibodies was evaluated according to Test Example 3. The results are shown in Table 5 and FIG. 5. Table 5 shows in vivo tumor accumulation of various antibodies (average of n=2).

TABLE 5

| | | | tumor-liver ratio | tumor-kidney ratio |
|---|---|---|---|---|
| humanized antibody (the present invention | example 3-1 | antibody 3 | 23.5 | 16.8 |
| | example 3-2 | antibody 4 | 11.7 | 12.7 |
| | example 3-3 | antibody 8 | 14.8 | 17.7 |
| | example 3-4 | antibody 9 | 20.5 | 15.4 |
| | example 3-5 | antibody 10 | 17.5 | 14.9 |
| | example 3-6 | antibody 16 | 18.1 | 14.0 |
| humanized antibody (patent document 3) | comparison example 3-1 | antibody 17 | 14.1 | 9.4 |
| | comparison example 3-2 | antibody 18 | 17.7 | 18.2 |
| | comparison example 3-3 | antibody 19 | 15.3 | 14.3 |

TABLE 5-continued

| | | | tumor-liver ratio | tumor-kidney ratio |
|---|---|---|---|---|
| chimeric antibody (patent document 1) | comparison example 3-4 | antibody 20 | 6.0 | 7.0 |

From these results of Table 5, it was clarified that the humanized antibody of the present invention (antibodies 3, 4, 8, 9, 10, 16) has a higher tumor-liver ratio and a higher tumor-kidney ratio than the chimeric antibody (antibody 20) of patent document 1; that is, a humanized antibody with high tumor accumulation was obtained. FIG. 5 shows time-course accumulation of Example 3-1 (antibody 3) with the highest tumor-liver ratio in Table 5. It was clarified that the antibody accumulates in the tumor in the lower right of the back of the mouse.

As described above, in general, since humanization of a chimeric antibody often reduces the binding activity to an antigen, in vivo tumor accumulation also decreases often. It is surprising that the humanized antibody of the present invention has been clarified to show far higher tumor accumulation than the chimeric antibody.

When production of an antibody-drug conjugate conjugated with a drug having a very high cell killing effect is assumed, high tumor accumulation of an antibody as a delivery tool therefor (i.e., the humanized antibody of the present invention) is very useful because it not only enhances the antitumor effect but also has the potential to reduce side effects on normal tissues.

INDUSTRIAL APPLICABILITY

In the present invention, a humanized antibody or an antigen-binding fragment thereof capable of binding to mucin subtype 5AC has been provided. The humanized antibody of the present invention has stable physical property as well as the binding ability to mucin subtype 5AC, and is superior in tumor accumulation. Therefore, the humanized antibody or an antigen-binding fragment thereof of the present invention is extremely useful for the treatment and/or diagnosis of cancer overexpressing mucin subtype 5AC, and further, production of antibody-drug conjugate for the treatment and/or diagnosis of cancer overexpressing mucin subtype 5AC.

This application is based on a patent application No. 2019-191560 filed in Japan (filing date: Oct. 18, 2019), the contents of which are incorporated in full herein.

The invention claimed is:

1. A non-conjugated humanized antibody capable of binding to mucin subtype 5AC, comprising:

a heavy chain variable region consisting of (1) an amino acid sequence having not less than 95% sequence identity with the amino acid sequence shown in SEQ ID NO: 1, (2) an amino acid sequence having not less than 95% sequence identity with the amino acid sequence shown in SEQ ID NO: 2, (3) an amino acid sequence having not less than 95% sequence identity with the amino acid sequence shown in SEQ ID NO: 3, or (4) an amino acid sequence having not less than 95% sequence identity with the amino acid sequence shown in SEQ ID NO: 4; and a light chain variable region consisting of (5) an amino acid sequence having not less than 95% sequence identity with the amino acid sequence shown in SEQ ID NO: 5, (6) an amino acid sequence having not less than 95% sequence identity with the amino acid sequence shown in SEQ ID NO: 6, (7) an amino acid sequence having not less than 95% sequence identity with the amino acid sequence shown in SEQ ID NO: 7, or (8) an amino acid sequence having not less than 95% sequence identity with the amino acid sequence shown in SEQ ID NO: 8, or an antigen-binding fragment thereof, wherein the sequence of the CDR regions of the heavy and light chains are not modified.

2. The humanized antibody or an antigen-binding fragment thereof according to claim 1, wherein the heavy chain variable region consists of (1) an amino acid sequence having not less than 98% sequence identity with the amino acid sequence shown in SEQ ID NO: 1, (3) an amino acid sequence having not less than 98% sequence identity with the amino acid sequence shown in SEQ ID NO: 3, or (4) an amino acid sequence having not less than 98% sequence identity with the amino acid sequence shown in SEQ ID NO: 4 and a light chain variable region consisting of (5) an amino acid sequence having not less than 98% sequence identity with the amino acid sequence shown in SEQ ID NO: 5, (6) an amino acid sequence having not less than 98% sequence identity with the amino acid sequence shown in SEQ ID NO: 6, (7) an amino acid sequence having not less than 98% sequence identity with the amino acid sequence shown in SEQ ID NO: 7, or, (8) an amino acid sequence having not less than 98% sequence identity with the amino acid sequence shown in SEQ ID NO: 8, or an antigen-binding fragment thereof.

3. The humanized antibody or an antigen-binding fragment thereof according to claim 1, comprising:

a heavy chain variable region consisting of (1) an amino acid sequence having not less than 99% sequence identity with the amino acid sequence shown in SEQ ID NO: 1, (3) an amino acid sequence having not less than 99% sequence identity with the amino acid sequence shown in SEQ ID NO: 3, or (4) an amino acid sequence having not less than 99% sequence identity with the amino acid sequence shown in SEQ ID NO: 4, and a light chain variable region consisting of (5) an amino acid sequence having not less than 99% sequence identity with the amino acid sequence shown in SEQ ID NO: 5, (6) an amino acid sequence having not less than 99% sequence identity with the amino acid sequence shown in SEQ ID NO: 6, (7) an amino acid sequence having not less than 99% sequence identity with the amino acid sequence shown in SEQ ID NO: 7, or (8) an amino acid sequence having not less than 99% sequence identity with the amino acid sequence shown in SEQ ID NO: 8.

4. The humanized antibody or an antigen-binding fragment thereof according to claim 1, comprising:

(1) a heavy chain variable region consisting of an amino acid sequence having not less than 98% sequence identity with the amino acid sequence shown in SEQ ID NO: 1, and (7) a light chain variable region consisting of an amino acid sequence having not less than 98% sequence identity with the amino acid sequence shown in SEQ ID NO: 7.

5. The humanized antibody, or an antigen-binding fragment thereof according to claim 1, comprising:

a heavy chain variable region consisting of the amino acid sequence shown in SEQ ID NO: 1, and a light chain variable region consisting of the amino acid sequence shown in SEQ ID NO: 7.

6. The humanized antibody according to claim 1, having an in vitro binding activity to mucin subtype 5AC comparable to or greater than that of a chimeric antibody.

7. A composition comprising:

the humanized antibody according to claim 1, or an antigen-binding fragment thereof.

8. A nucleic acid encoding the humanized antibody according to claim 1.

9. An expression vector, comprising:

the nucleic acid according to claim 8.

10. A host cell comprising:

the expression vector according to claim 9.

11. A method for producing a non-conjugated humanized antibody or an antigen-binding fragment thereof in the host cell according to claim 10, comprising:

inserting a nucleic acid encoding the humanized antibody or an antigen-binding fragment thereof into an expression vector, introducing the nucleic acid containing expression vector into a host cell; culturing the host cell containing the expression vector, and isolating the humanized antibody or an antigen-binding fragment thereof from a culture supernatant of the host cell by chromatographic purification.

12. An in vitro method for evaluating an expression level of mucin subtype 5AC in a cell or a tissue sample, comprising:

contacting the cell or tissue sample with a humanized antibody or an antigen-binding fragment thereof of claim 1, wherein the antibody or fragment thereof is labeled;

detecting the labeled humanized antibody or an antigen-binding fragment in the cell or tissue sample, thereby generating a signal; and evaluating an expression level of mucin subtype 5AC expressed in the cell or tissue sample based on the signal.

13. An in vitro method for measuring a volume of a cancer overexpressing mucin subtype 5AC in a subject, comprising:

contacting a tissue sample of the subject and a tissue sample of a healthy subject with a humanized antibody or an antigen-binding fragment thereof of claim 1, wherein the antibody or fragment thereof is labeled;

detecting the labeled humanized antibody or an antigen-binding fragment in the tissue sample of the subject, thereby generating a first signal;

detecting the labeled humanized antibody or an antigen-binding fragment in the tissue sample of the healthy subject, thereby generating a second signal;

comparing the first signal and the second signal, wherein the comparison correlates to a volume of the cancer present in the subject.

14. An in vitro method for measuring a volume of a cancerous tissue overexpressing mucin subtype 5AC in a subject, comprising:

contacting a tissue sample of the subject with a humanized antibody or an antigen-binding fragment thereof of claim 1, wherein the antibody or fragment thereof is labeled;

detecting the labeled humanized antibody or an antigen-binding fragment in the tissue sample of the subject, thereby generating a signal; and calculating the volume of a cancerous tissue volume based on the signal intensity.

15. A kit for the in vitro diagnosis of a cancer overexpressing mucin subtype 5AC comprising the humanized antibody or an antigen-binding fragment thereof of claim 1, and a label for detecting the antibody or an antigen-binding antibody fragment thereof.

* * * * *